United States Patent
Ohnishi et al.

(10) Patent No.: US 9,013,703 B2
(45) Date of Patent: Apr. 21, 2015

(54) GAS ANALYZING APPARATUS

(71) Applicant: Horiba, Ltd., Kyoto (JP)

(72) Inventors: Toshikazu Ohnishi, Kyoto (JP);
Toshiyuki Tsujimoto, Kyoto (JP)

(73) Assignee: Horiba, Ltd., Kyoto (JP)

( * ) Notice: Subject to any disclaimer, the term of this patent is extended or adjusted under 35 U.S.C. 154(b) by 217 days.

(21) Appl. No.: 13/723,338

(22) Filed: Dec. 21, 2012

(65) Prior Publication Data
US 2013/0161544 A1    Jun. 27, 2013

(30) Foreign Application Priority Data
Dec. 27, 2011   (JP) ................. 2011-286647
Dec. 27, 2011   (JP) ................. 2011-286706

(51) Int. Cl.
G01N 21/00   (2006.01)
G01N 21/85   (2006.01)
G01N 21/15   (2006.01)
G01N 21/53   (2006.01)

(52) U.S. Cl.
CPC ............. G01N 21/85 (2013.01); G01N 21/15 (2013.01); G01N 21/8507 (2013.01); G01N 2021/536 (2013.01)

(58) Field of Classification Search
CPC ....... G01N 21/85; G01N 21/15; G01N 21/59; G01N 21/00; G01N 21/84
USPC ............................. 356/437–438, 432; 250/564
See application file for complete search history.

(56) References Cited

U.S. PATENT DOCUMENTS

| | | | |
|---|---|---|---|
| 4,549,080 A | | 10/1985 | Baskins et al. |
| 5,222,389 A | * | 6/1993 | Wong .................... 73/31.02 |
| 5,684,296 A | * | 11/1997 | Hamblin et al. ......... 250/227.11 |
| 5,781,306 A | | 7/1998 | Hartig et al. |
| 7,488,449 B2 | * | 2/2009 | Kempe .................... 422/502 |
| 7,817,277 B2 | * | 10/2010 | Crist et al. ............... 356/436 |
| 2012/0033218 A1 | * | 2/2012 | Hokamura et al. ......... 356/432 |
| 2012/0033219 A1 | * | 2/2012 | Hokamura et al. ......... 356/438 |

FOREIGN PATENT DOCUMENTS

| | | |
|---|---|---|
| EP | 1284419 A1 | 2/2003 |
| WO | 2011066868 A1 | 6/2011 |

OTHER PUBLICATIONS

Extended European Search Report dated Apr. 8, 2012, Application No. 12008569.1-1554.

* cited by examiner

*Primary Examiner* — Tarifur Chowdhury
*Assistant Examiner* — Isiaka Akanbi
(74) *Attorney, Agent, or Firm* — Brooks Kushman P.C.

(57) ABSTRACT

A gas analyzing apparatus includes a probe for measuring a concentration of sample gas flowing in a pipe by an optical measurement system. Influence of a thermal lens effect phenomenon is suppressed so that measurement accuracy is improved. The apparatus includes a probe tube disposed to cross a flow path of the sample gas in the pipe to introduce the sample gas flowing in the pipe to a predetermined hollow measurement region. A light emission portion and a light receiving portion for project measurement light to the measurement region in the probe tube and receive the measurement light after passing through the sample gas in the measurement region. A purge gas feed tube disposed in the probe tube supplies purge gas to a region between the optical system members and the measurement region, with a gap to the inner wall surface of the probe tube.

11 Claims, 14 Drawing Sheets

GAS ANALYZING APPARATUS

CROSS-REFERENCE TO RELATED APPLICATIONS

This application claims priority under 35 U.S.C. §119 to Japanese Patent Application Nos. 2011-286706 and 2011-286647 filed on Dec. 27, 2011. The entire disclosure of Japanese Patent Application Nos. 2011-286706 and 2011-286647 is hereby incorporated herein by reference.

BACKGROUND

1. Field of the Invention

The present invention relates to a gas analyzing apparatus, and particularly to the gas analyzing apparatus that emits and receives measurement light into sample gas flowing in a pipe so as to analyze concentration of a predetermined component.

2. Description of the Related Art

Flue gas exhausted from a boiler burning coal or heavy oil contains components such as sulfur oxide (SOx), nitrogen oxide (NOx), carbon dioxide ($CO_2$), carbon monoxide (CO), and the like.

As a gas analyzing apparatus for analyzing content of each component contained in the gas, for example, there is an apparatus in which a probe is disposed in a gas flow path in the pipe so as to cross the same, measurement light emitted from a light source toward the gas is reflected by a reflector disposed at the tip of the probe, and hence concentration of components of the sample gas is analyzed based on information of the reflected measurement light (as shown in U.S. Pat. No. 5,781,306, for example).

FIG. 14 is a cross-sectional view schematically illustrating probes used for a conventional gas analyzing apparatus.

A probe A illustrated in FIG. 14 includes a probe tube B having a hollow tube shape in which the measurement light passes through. The probe tube B is attached to a pipe side wall D so that the probe tube B crosses the gas flow path in a flue C.

The pipe side wall D has an attachment portion E for attaching the probe A. The probe A is attached to the attachment portion E via a flange F.

In the proximal end portion of the probe A, there are disposed a light emission portion G for emitting measurement light into the probe tube B and a light receiving portion H for receiving reflection light. In the distal end portion of the same, there is disposed a reflector I for reflecting the measurement light from the light emission portion G to the light receiving portion H.

In the gas analyzing apparatus using the probe A as described above, gas in the flue C is led into the probe tube B, the measurement light emitted from the light emission portion G and reflected by the reflector I is received by the light receiving portion G. Thus, it is possible to analyze each component in the gas based on characteristics of the measurement light.

When the sample gas flowing in the flue C is led into the probe tube B, if the sample gas reaches an optical system member such as the light emission portion G, the light receiving portion H, or the reflector I via the probe tube B, the optical system member is exposed to the sample gas at high temperature and may be damaged by dust pollution or corrosion.

Therefore, in order to prevent the optical system members from being exposed to the high temperature sample gas, a purge gas feed portion J is disposed on the probe A, and purge gas is fed between a measurement region of the probe tube B and the light emission portion G as well as the light receiving portion H.

In addition, it is possible to adopt a structure in which the purge gas is fed into the distal end portion of the probe tube B through a purge gas feed tube (not shown) disposed in the probe tube B so that the reflector I can be prevented from being exposed to the sample gas.

In this structure of the probe A, there may be formed a gap K communicating directly to the flue C between the probe tube B and the attachment portion E.

In a case where the gas flowing in the flue C is flue gas, the temperature thereof is 100 to 400 degrees centigrade, and the gas flow rate is 5 to 25 m/sec. Therefore, if a part of the gas flowing in the flue C flows into the gap K, it is cooled in the gap by the purge gas led into the probe tube B at the outside air temperature. As a result, there occurs a difference of gas temperature between the upstream side in the vicinity of the gap and the downstream side.

If unevenness of ambient gas temperature occurs in this way, the temperature of the probe tube B becomes uneven, and particularly in a probe of the optical system having the hollow space in which the measurement light passes through, thermal lens effect phenomenon may occur.

Thus, there may occur a problem that the measurement optical axis fluctuates or is shifted due to an influence of the thermal lens effect phenomenon, and there is a problem that the light receiving state in the light receiving portion becomes unstable so that the measurement accuracy is deteriorated.

SUMMARY

A gas analyzing apparatus for measuring concentration of a gas flowing in the pipe by an optical measurement system may prevent occurrence of a thermal lens effect phenomenon due to unevenness of temperature distribution so that measurement accuracy is improved.

Hereinafter, a plurality of embodiments are described that include various aspects for solving the problem. These embodiments can be arbitrarily combined as necessary.

A gas analyzing apparatus according to an aspect of the present invention includes a tube-like member, an optical system member, a purge gas feed portion, and a blocking plate.

The tube-like member includes a light path through which measurement light is emitted to a predetermined measurement region of sample gas flowing in a pipe and/or through which the measurement light from the measurement region is received. The tube-like member is attached so as to penetrate a pipe side wall. The optical system member is configured to emit the measurement light to the sample gas in the measurement region and/or to receive the measurement light from the measurement region. The purge gas feed portion is configured to supply purge gas to a region positioned on a light path of the measurement light between the optical system member and the measurement region. At least one blocking plate is disposed at a position so as to suppress the sample gas from flowing into a gap between the tube-like member and the pipe side wall.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

First Embodiment

Figure 1:
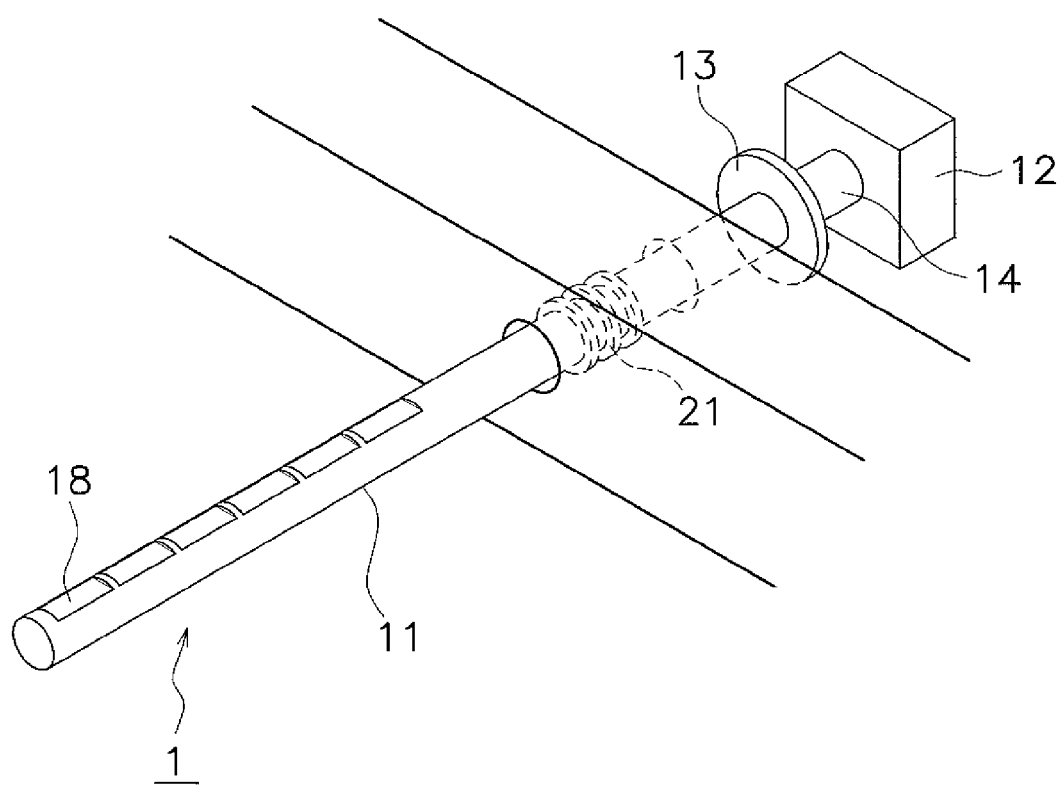
FIG. 1 is a perspective view of a gas analyzing apparatus of a first embodiment.
Figure 2:
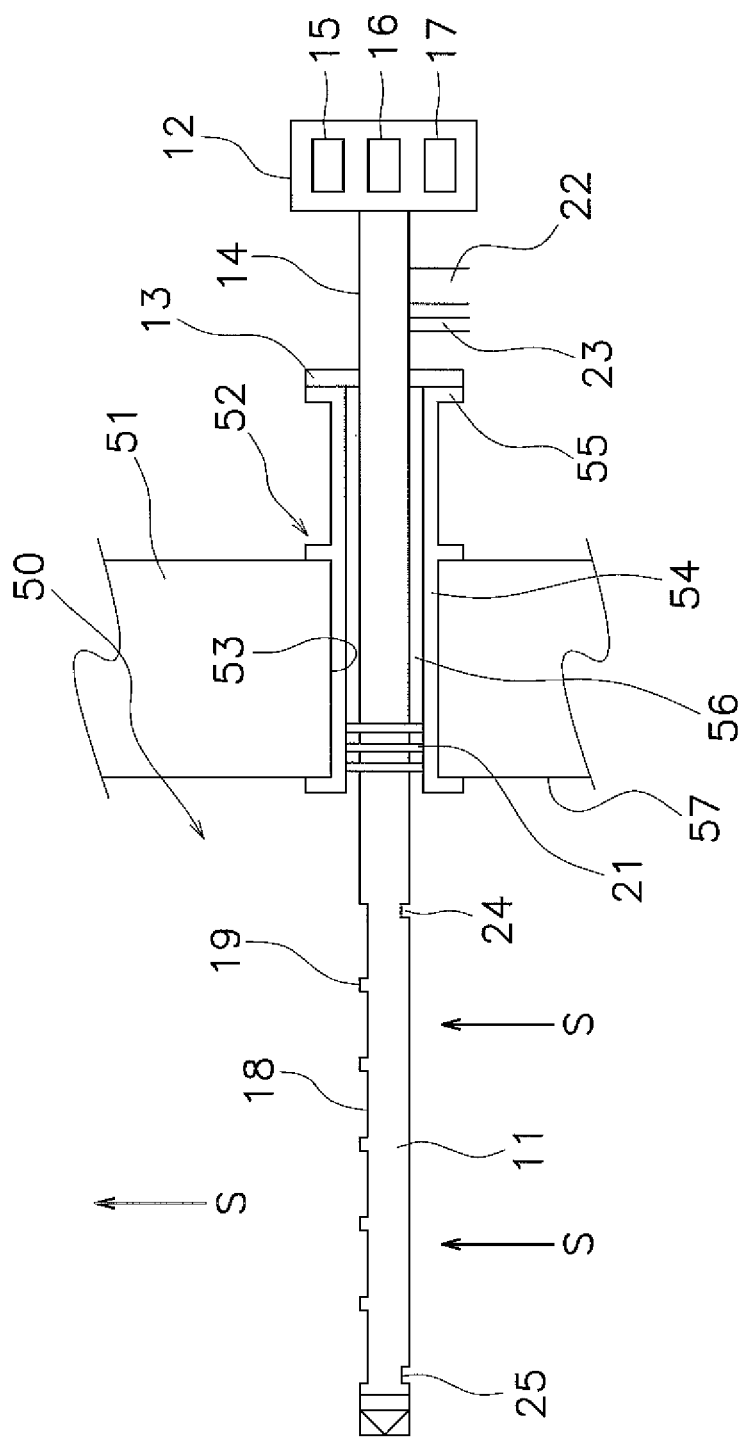
FIG. 2 is a side view of the gas analyzing apparatus of the first embodiment.

FIG. 1 is a perspective view illustrating a structure of a gas analyzing apparatus 1 according to a first embodiment, and FIG. 2 is a side view of the same.

The gas analyzing apparatus 1 includes a probe tube 11 (an example of a tube-like member), an analyzing unit 12, a flange 13, and a light guide tube 14.

The analyzing unit 12 includes a light emission portion 15, a light receiving portion 16, and a control unit 17.

The light emission portion 15 is a light source that emits a laser beam as measurement light toward gas to be measured via the light guide tube 14 and the probe tube 11. The light emission portion 15 can be constituted of an infrared laser generation apparatus or the like for emitting light having high straightness in a predetermined wavelength band.

The light receiving portion 16 is a light receiving element that receives the measurement light entering through the gas to be measured in the flue.

The control unit 17 controls emission of the laser beam from the light emission portion 15 so as to analyze components of the gas to be measured based on the measurement light received by the light receiving portion 16.

The analyzing unit 12 is connected to the probe tube 11 via the light guide tube 14 and the flange 13.

The probe tube 11 is formed in a hollow cylindrical shape and is disposed so as to be perpendicular to the gas flow S in a flue 50 formed inside the pipe side wall 51.

In the measurement region of the probe tube 11, there is formed openings 18 positioned on the downstream side of the gas flow S for leading the gas into the probe tube 11. In the illustrated example, a plurality of ribs 19 are disposed in the opening 18 so that strength of the probe tube 11 is maintained.

The shape of the opening 18s and the number of the ribs 19 are not limited to those in the illustrated example.

In a distal end portion of the probe tube 11, there is disposed a reflector 20 for reflecting the measurement light emitted from the light emission portion 15 of the analyzing unit 12.

The reflector 20 is used for reflecting the measurement light emitted from the light emission portion 15 to the light receiving portion 16, and can be constituted of a corner-cube prism.

The gas analyzing apparatus 1 is attached to an attachment portion 52 of the pipe side wall 51 (an example of the pipe side wall) constituting the flue 50.

The attachment portion 52 can be constituted of an installation pipe 54 (an example of the tube-like inner wall surface) attached to the opening 53 of the pipe side wall 51, for example.

The installation pipe 54 is a cylindrical member having an inner diameter larger than an outer diameter of the probe tube 11 of the gas analyzing apparatus 1 and is fixed to the pipe side wall 51 by means of welding or screwing.

In addition, the installation pipe 54 includes an attachment flange 55 for fixing the gas analyzing apparatus 1. By welding or screwing the flange 13 of the gas analyzing apparatus 1 to the attachment flange 55, the gas analyzing apparatus 1 is indirectly fixed to the pipe side wall 51.

It is preferred that the inner diameter of the installation pipe 54 should be adjusted to the outer diameter of the probe tube 11 to be received inside the same so that no gap occurs between them. However, if the existing installation pipe 54 is used when replacing with a different standard type, a gap 56 (an example of the gap) may occur between the probe tube 11 and the installation pipe 54.

In addition, considering a case where the probe tube 11 is exchanged or a case where the gas analyzing apparatus 1 itself is exchanged, it is considered to install the installation pipe 54 having a little larger inner diameter for a margin in advance. In this case too, there occurs the gap 56 between the probe tube 11 and the installation pipe 54.

In order to prevent a part of the gas flow S flowing in the flue 50 from flowing in through the gap 56 between the probe tube 11 and the installation pipe 54, there is disposed a blocking plate 21 (an example of the blocking plate).

The blocking plate 21 is disposed at a position close to an inner surface 57 of the pipe side wall 51 (an example of the inner surface of the pipe side wall). In this way, since the blocking plate 21 is disposed on the flue 50 side, the sample gas is prevented from flowing into the gap 56.

In this apparatus, the sample gas is less likely to flow into the periphery of the probe tube 11 located in the pipe side wall 51 by providing the blocking plate 21. Therefore, without separately providing a functional unit, such as a heater or a temperature control system, it is possible to maintain a uniform temperature in the radial cross section of the probe tube 11, and as a result, it is possible to prevent a decrease in measurement accuracy due to the thermal lens effect phenomenon.

The blocking plate 21 is a disk-like member fixed to the outer circumference surface of the probe tube 11, and the outer circumference rim is close to or contacts with the inner circumferential surface of the installation pipe 54. In the former close case, it is preferred that the gap should be small from a viewpoint of shielding the sample gas. In addition, in the latter contacting case, the gap 56 is shielded so that the effect of blocking the sample gas is enhanced.

In the illustrated example, the three blocking plates 21 are disposed with predetermined spaces along the length direction of the probe tube 11. In this way, because a plurality of blocking plates 21 are disposed with a space between each other along the axis direction of the probe tube 11, the sample gas hardly flows into the gap 56.

In this apparatus, the blocking plates 21 are fixed to the probe tube 11, and the blocking plates 21 move together with the probe tube 11. Therefore, it is not necessary to add special work and structure for installing and removing the blocking plates 21.

The gap 56 between the probe tube 11 and the installation pipe 54 reaches a vicinity of the outer surface of the pipe side wall 51. Therefore, if a part of the gas flow into the flue 50 at a temperature of 100 to 400 degrees centigrade flows into the gap 56 and reaches a vicinity of the outer surface of the pipe side wall 51, it is cooled in accordance with a temperature difference compared to the outside air temperature. However, in this embodiment, since the protruding blocking plates 21 are disposed on the outer surface of the probe tube 11, it is possible to prevent a part of the gas flow from flowing into the gap 56, and hence the unevenness of temperature distribution does not occur in the probe tube 11.

In the illustrated example, the blocking plate 21 is disposed at a position a little apart from the inner surface 57 of the pipe side wall 51. Since the blocking plate 21 is disposed at a vicinity of the inner surface 57 of the pipe side wall 51, the unevenness of the temperature distribution hardly occurs.

In addition, the blocking plate 21 suppresses convection of air layers in the thickness direction of the pipe side wall 51. Therefore, it is possible to suppress a temperature variation in the vicinity of the attachment portion 52. As illustrated in the diagram, if three blocking plates 21 are disposed at predetermined spaces in the thickness direction of the pipe side wall 51, three thermal insulating layers are formed so that convection of the air layers can be suppressed more.

Note that three blocking plates 21 are disposed in this example, but this is not a limitation. It is possible to dispose one or two blocking plates 21 so that the above-mentioned effect can be obtained, and further it is possible to dispose four or more blocking plates 21.

Further, the blocking plate 21 may have a block-like shape having a predetermined thickness in the thickness direction of the pipe side wall 51.

The blocking plate 21 may be constituted of the same metal material as the probe tube 11 having high heat resistance and corrosion resistance, and can be fixed to the outer surface of the probe tube 11 by means of welding or screwing.

The probe tube 11 is fixed to the flange 13 and is supported as a cantilever. Therefore, if the outer diameter of the blocking plates 21 is set to be substantially the same as the inner diameter of the installation pipe 54, a middle part of the probe tube 11 can be stably supported by contact between the blocking plates 21 and the installation pipe 54. Therefore, by disposing the blocking plates 21 on the probe tube 11, it is also possible to prevent vibration of the probe tube 11 disposed in the gas flow S.

Note that the purge gas is supplied from both ends of the measurement region of the probe tube 11 through the purge gas feed portions 22 and 23 in this example.

The purge gas is supplied for preventing the optical members such as the light emission portion 15, the light receiving portion 16, and the reflector 20 from being exposed to the sample gas. The purge gas supplied from the first purge gas feed portion 22 is supplied to the probe tube 11 via the light guide tube 14. In addition, the purge gas supplied from the purge gas feed portion 23 is supplied to the distal end portion of the probe tube 11 through the purge gas feed tube (not shown) disposed in the light guide tube 14 and the probe tube 11.

The notch holes 24 and 25 are disposed on the upstream side positioned at both ends of the measurement region of the probe tube 11.

The purge gas supplied from the first purge gas feed portion 22 to the inside of the probe tube 11 is prevented from flowing into the measurement region side in the probe tube 11 by the gas flow S flowing in through the notch hole 24 of the probe tube 11 to the downstream side, and hence a measurement error due to the purge gas does not occur in the measurement region. In addition, the purge gas supplied from the purge gas feed portion 22 can prevent the gas flow S entering through the notch hole 24 from flowing into the analyzing unit 12 side. Thus, it is possible to prevent pollution and corrosion of optical systems such as the light emission portion 15 and the light receiving portion 16.

Since the purge gas supplied from the second purge gas feed portion 23 to the distal end side of the probe tube 11 is prevented from flowing into the measurement region side in the probe tube 11 by the gas flow S entering through the notch hole 25 of the probe tube 11 to flow to the downstream side, a measurement error due to the purge gas does not occur in the measurement region. In addition, since the purge gas supplied from the purge gas feed portion 23 can prevent the gas flow S entering through the notch hole 25 from flowing into the reflector 20 side, pollution and corrosion of the reflector 20 can be prevented.

As described above, the first embodiment shows the example of the gas analyzing apparatus for performing reflection type optical system measurement.

When performing the reflection optical system measurement, the analysis is performed based on the measurement light that is emitted from the light emission portion 15, passes through the inside of the probe tube 11, is reflected by the reflector 20, passes through the inside of the probe tube 11 again, and is received by the light receiving portion 16.

Therefore, the measurement light emitted from the light emission portion 15 to be received by the light receiving portion 16 passes through the vicinity of the attachment portion 52 two times. Since the blocking plates 21 are disposed, unevenness of temperature distribution does not occur. Therefore, the measurement accuracy can be maintained to be high, and hence it is possible to easily perform optical axis adjustment upon installation in short time.

The shape of the probe tube 11 is not limited to the above-mentioned structure, as long as a structure having a hollow part through which the measurement light can pass is employed. The cross section thereof may have a polygonal shape, an ellipse shape, or a combined shape thereof.

Second Embodiment

Figure 3:
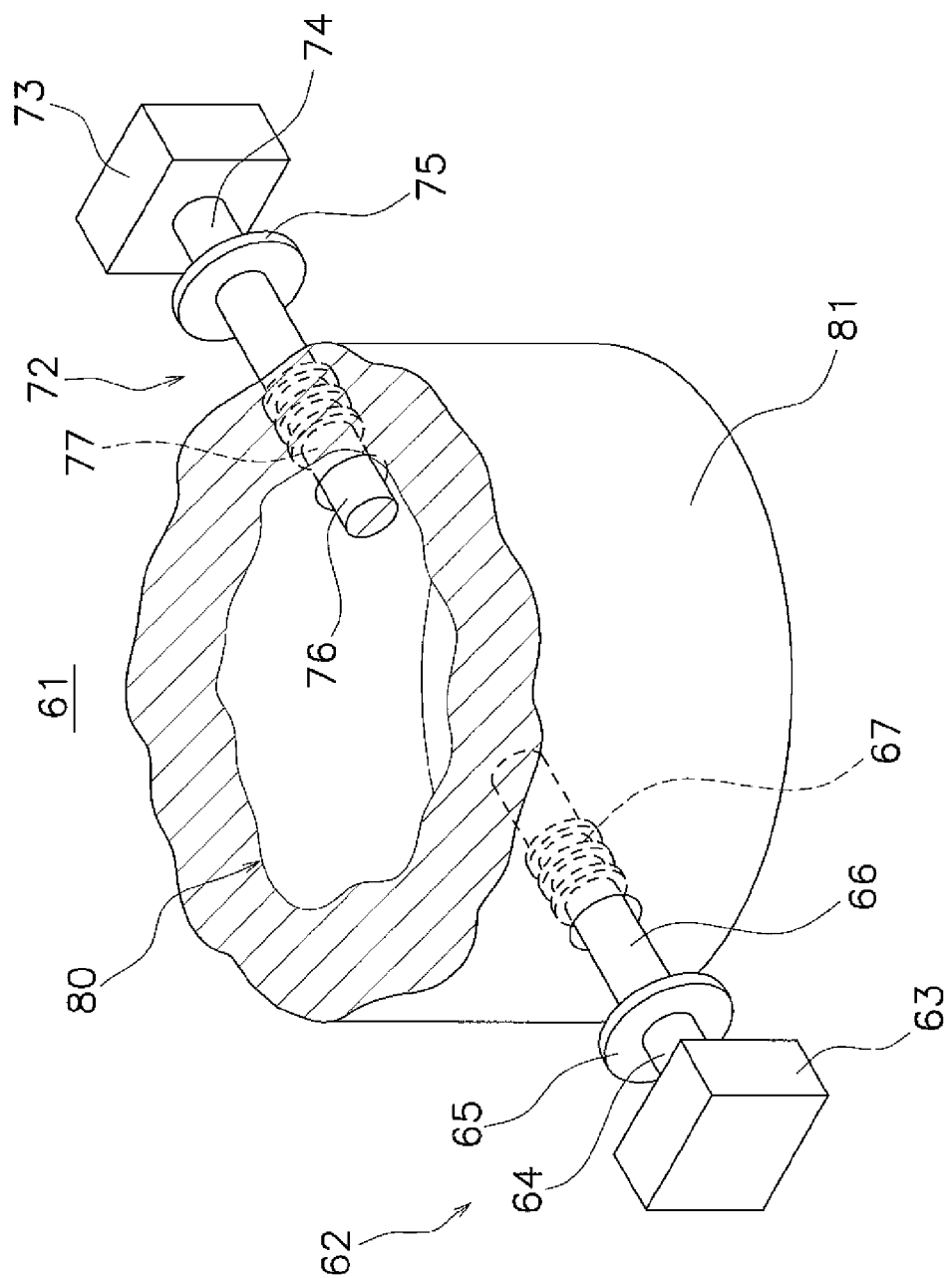
FIG. 3 is a perspective view of a second embodiment.
Figure 4:
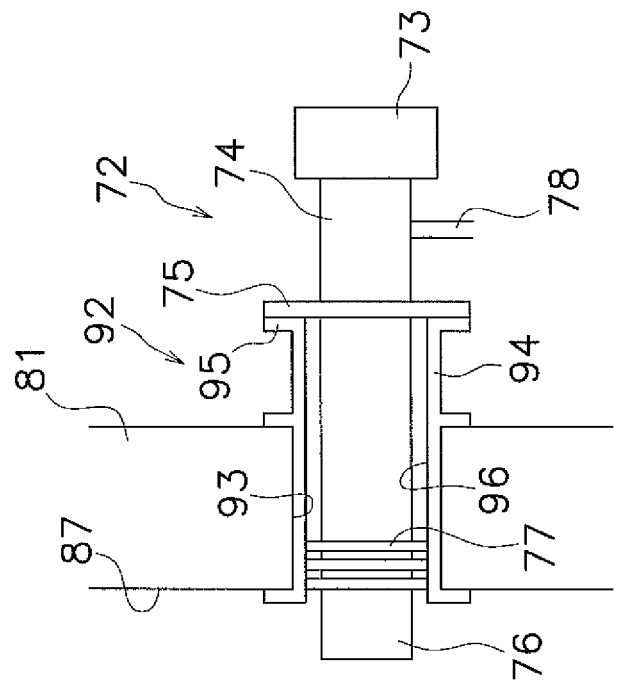
FIG. 4 is a side view of the second embodiment.
Figure 4:
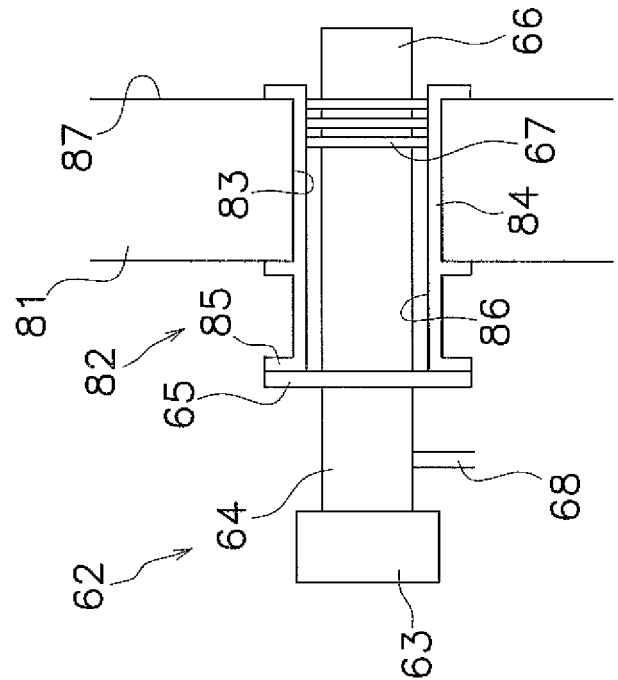

FIG. 3 is a perspective view of a gas analyzing apparatus according to a second embodiment, and FIG. 4 is a side view of the same.

A gas analyzing apparatus 61 according to the second embodiment is a transmission type gas analyzing apparatus in which the light emission portion and the light receiving portion are disposed at opposed positions, and includes a light emission portion unit 62 and a light receiving portion unit 72.

The light emission portion unit 62 includes a light emission portion 63, a first light guide tube 64, a first flange 65, and a first sleeve 66 (an example of the tube-like member).

The light emission portion 63 is a light source that emits a laser beam as the measurement light toward the gas to be measured through the first light guide tube 64 and the first sleeve 66, and can be constituted of an infrared laser generation apparatus or the like for emitting light having high straightness in a predetermined wavelength band.

The first sleeve 66 has a hollow cylindrical shape, and is disposed so as to be perpendicular to the gas flow S in a flue 80 formed inside a pipe side wall 81.

A purge gas feed portion 68 is disposed on the light emission portion unit 62, and the purge gas is supplied to the first sleeve 66 via the purge gas feed portion 68.

The purge gas is supplied for preventing the optical system member of the light emission portion 63 from being exposed to the sample gas. The purge gas supplied from the purge gas feed portion 68 is supplied to the first sleeve 66 through the first light guide tube 64.

The purge gas supplied to the first sleeve 66 flows into the flue 80 together with the sample gas in the distal end portion of the first sleeve 66. Thus, it is possible to prevent the sample gas flowing in the flue 80 from flowing into the light emission portion 63 side.

The light emission portion unit 62 is attached to a first attachment portion 82 of the pipe side wall 81 (an example of the pipe side wall) constituting the flue 80.

The first attachment portion 82 can be constituted of a first installation pipe 84 (an example of the tube-like inner wall surface) attached to an opening 83 of the pipe side wall 81, for example.

The first installation pipe 84 is a cylindrical member having an inner diameter larger than the outer diameter of the first sleeve 66 and is fixed to the pipe side wall 81 by means of welding or screwing.

In addition, the first installation pipe 84 is equipped with a first attachment flange 85 for fixing the light emission portion unit 62. When the first flange 65 of the light emission portion unit 62 is welded or screwed to this first attachment flange 85, the light emission portion unit 62 is indirectly fixed to the pipe side wall 81.

It is preferred that the inner diameter of the first installation pipe 84 should be adjusted to the outer diameter of the first sleeve 66 to be received inside the same so that no gap occurs between them. However, if the existing first installation pipe 84 is used when replacing with a different standard type, a gap 86 (an example of the gap) may occur between the first sleeve 66 and the first installation pipe 84.

In addition, considering a case where the first sleeve 66 is exchanged or a case where the light emission portion unit 62 itself is exchanged, it is considered to install the first installation pipe 84 having a little larger inner diameter for a margin in advance. In this case too, there occurs the gap 86 between the first sleeve 66 and the first installation pipe 84.

In order to prevent a part of the gas flow S flowing in the flue 80 from flowing into the gap 86 between the first sleeve 66 and the first installation pipe 84, a blocking plate 67 (an example of the blocking plate) is disposed.

The blocking plates 67 are disposed in the vicinity of an inner surface 87 of the pipe side wall 81 (an example of the inner surface of the pipe side wall). In this way, because the blocking plates 67 are disposed on the flue 80 side, it is possible to prevent the sample gas from flowing into the gap 86.

The blocking plate 67 is a disk-like member fixed to the outer circumference surface of the first sleeve 66, and the outer circumference rim is close to or contacts with the inner circumferential surface of the first installation pipe 84. In the former close case, it is preferred that the gap should be small from viewpoint of shielding the sample gas. Since there is a gap between the outer circumference rim of the blocking plate 67 and the inner circumferential surface of the first installation pipe 84, the first sleeve 66 can be easily removed so that calibration can be easily performed. In addition, in the latter contact case, the gap 86 is shielded so that the effect of blocking the sample gas is enhanced.

In the illustrated example, the three blocking plates 67 are disposed with a predetermined space with each other along the length direction of the first sleeve 66. In this way, because a plurality of blocking plates 67 are disposed with spaces in the axis direction of the first sleeve 66, the sample gas hardly flows into the gap 86.

The light receiving portion unit 72 includes a light receiving portion 73, a second light guide tube 74, a second flange 75, and a second sleeve 76 (an example of the tube-like member).

The light receiving portion 73 is a light receiving element that receives the measurement light entering through the gas to be measured in the flue.

The light receiving portion 73 may further include an analyzing unit that performs gas analysis such as calculation of concentration of the sample gas based on the measurement light received by the light receiving element. It is also possible to adopt a structure further including a control unit connected to the light emission portion unit 62 by wireless or wired means so as to control the light emission portion 63 and the light receiving portion 73.

The second sleeve 76 is formed in a hollow cylindrical shape, and is disposed so as to be perpendicular to the gas flow S in the flue 80 formed inside the pipe side wall 81.

The light receiving portion unit 72 is provided with a purge gas feed portion 78, and the purge gas is supplied to the second sleeve 76.

The purge gas is supplied so that optical system members of the light receiving portion 73 are not exposed to the sample gas. The purge gas supplied from the purge gas feed portion 78 is supplied to the second sleeve 76 via the second light guide tube 74.

The purge gas supplied to the second sleeve 76 flows into the flue 80 together with the sample gas in the distal end portion of the second sleeve 76. Thus, it is possible to prevent the sample gas flowing in the flue 80 from flowing into the light receiving portion 73 side.

The light receiving portion unit 72 is attached to a second attachment portion 92 of the pipe side wall 81 (an example of the pipe side wall) constituting the flue 80.

The second attachment portion 92 is disposed at a position opposed to the first attachment portion 82, and can be constituted of a second installation pipe 94 (an example of the tube-like inner wall surface) attached to an opening 93 of the pipe side wall 81, for example.

The second installation pipe 94 is a cylindrical member having an inner diameter larger than the outer diameter of the second sleeve 76, and is fixed to the pipe side wall 81 by means of welding or screwing.

In addition, the second installation pipe 94 includes a second attachment flange 95 for fixing the light receiving portion unit 72. When the second flange 75 of the light receiving portion unit 72 is welded or screwed to this second attachment flange 95, the light receiving portion unit 72 is indirectly fixed to the pipe side wall 81.

A gap 96 (an example of the gap) is defined between the second sleeve 76 and the second installation pipe 94 similarly to the light emission portion unit 62 side. Blocking plates 77 are disposed on the outer surface of the second sleeve 76 so as to prevent a part of the gas flow S flowing in the flue 80 from flowing into the gap 96.

The blocking plates 77 suppress the sample gas from entering into the gap 96 similarly to the blocking plates 67.

In this gas analyzing apparatus 61, the purge gas is supplied to the first sleeve 66 and the second sleeve 76 so as to prevent optical system members of the light emission portion 63 and the light receiving portion 73 from being exposed to the sample gas flowing in the flue 80. In addition, the region to be measured can be specified to a region between the distal ends of the first sleeve 66 and the second sleeve 76.

In the case described above, blocking plates 67 and 77 are respectively disposed on the first sleeve 66 and the second sleeve 76 in order to prevent a part of the sample gas flowing in the flue 80 from flowing in the gap between the first sleeve 66 and the first installation pipe 84 as well as in the gap between the second sleeve 76 and the second installation pipe 94.

Thus, temperature distribution on the upstream side and the downstream side of the sample gas becomes uniform, and hence temperature distribution in the first sleeve 66 and the second sleeve 76 also becomes uniform. Therefore, it is possible to reduce the thermal lens effect phenomenon so that measurement accuracy can be improved. In addition, optical axis adjustment upon installation can be easily performed in short time.

Third Embodiment

Figure 5:
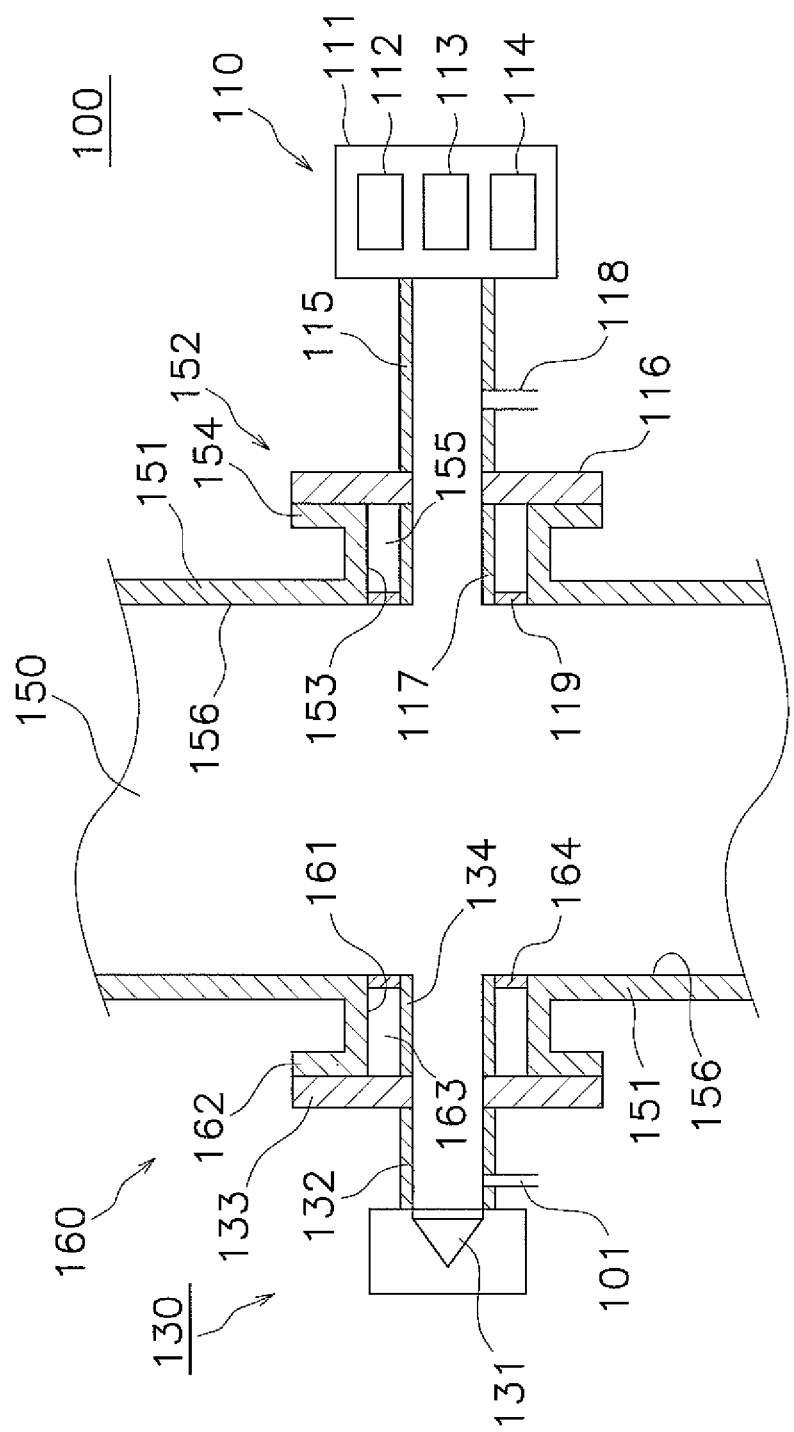
FIG. 5 is a cross-sectional side view of a gas analyzing apparatus of a third embodiment.

FIG. 5 is a side cross-sectional view of a gas analyzing apparatus 100 according to a third embodiment.

The gas analysis apparatus 100 according to the third embodiment is a transmission-type gas analyzer having a light emitting unit and a light receiving portion disposed at opposite positions. The apparatus comprises at least one blocking plate 119, 164 located near the inner surface of the pipe side wall 151 in each of the light emitting portion and the light receiving portion.

The gas analyzing apparatus 100 includes a first unit 110 and a second unit 130 disposed at opposed positions with respect to the pipe side wall 151.

The first unit 110 includes an analyzing unit 111, a first light guide tube 115, a first flange 116, and a first sleeve 117 (an example of the tube-like member).

The analyzing unit 111 includes a light emission portion 112, a light receiving portion 113, and a control unit 114.

The light emission portion 112 is a light source emitting a laser beam as the measurement light through the first light guide tube 115 and the first sleeve 117 to the gas to be measured. The light emission portion 112 can be constituted of an infrared laser generation apparatus for emitting light in a predetermined wavelength band having high straightness.

The light receiving portion 113 is a light receiving element that receives the measurement light entering through the gas to be measured in the flue.

The control unit 114 controls the laser beam emission from the light emission portion 112 and analyzes components of the gas to be measured based on the measurement light received by the light receiving portion 113.

The analyzing unit 111 is connected to the first sleeve 117 via the first light guide tube 115 and the first flange 116.

The first sleeve 117 is formed in a hollow cylindrical shape so as to provide a path of the measurement light emitted from the light emission portion 112, and also works as a path guiding the purge gas.

In the first light guide tube 115 of the first unit 110, there is disposed a purge gas feed portion 118. Through the purge gas feed portion 118, the purge gas is supplied to the first sleeve 117.

The purge gas is supplied for preventing the optical system members of the light emission portion 112 and the light receiving portion 113 from being exposed to the sample gas.

The purge gas supplied from the purge gas feed portion 118 is supplied to the first sleeve 117 via the first light guide tube 115.

The purge gas supplied to the first sleeve 117 flows into a flue 150 together with the sample gas in the distal end portion of the first sleeve 117. Thus, it is possible to prevent the sample gas flowing in the flue 150 from flowing into the analyzing unit 111 side.

The first unit 110 is attached to a first attachment portion 152 of a pipe side wall 151 (an example of the pipe side wall) constituting the flue 150.

The first attachment portion 152 includes a first attachment flange 154 that is disposed on an opening 153 of the pipe side wall 151 (an example of the tube-like inner wall surface), for example.

A blocking plate 119 (an example of the blocking plate) is attached so as to shield between the opening 153 of the first attachment portion 152 and a gap 155 (an example of the gap) of the first sleeve 117.

The blocking plate 119 is disposed at the vicinity of an inner surface 156 of the pipe side wall 151 (an example of the inner surface of the pipe side wall). In this way, because the blocking plate 119 is disposed on the flue 150 side, the sample gas is prevented from flowing into the gap 155.

The blocking plate 119 is a disk-like member fixed to the outer circumference surface of the first sleeve 117, and the outer circumference rim thereof is close to or contacts with the inner circumferential surface of the opening 153. In the former close case, it is preferred that the gap should be small from a viewpoint of shielding the sample gas. In addition, in the latter contacting case, the gap 155 is shielded so that the effect of blocking the sample gas is enhanced.

The second unit 130 includes a reflector 131, a second light guide tube 132, a second flange 133, and a second sleeve 134.

The reflector 131 reflects the measurement light emitted from the light emission portion 112 to the light receiving portion 113 side, and can be constituted of a corner-cube prism.

The reflector 131 is connected to the second sleeve 134 via the second light guide tube 132 and the flange 133.

The second sleeve 134 is formed in a hollow cylindrical shape, provides a path of the measurement light emitted from the light emission portion 112, and also works as a path guiding the purge gas.

A purge gas feed portion 101 is disposed in the second light guide tube 132 of the second unit 130, and the purge gas is supplied to the second sleeve 134 via the purge gas feed portion 101.

The purge gas is supplied for preventing the reflector 131 from being exposed to the sample gas. The purge gas supplied from the purge gas feed portion 101 is supplied to the second sleeve 134 via the second light guide tube 132.

The purge gas supplied to the second sleeve 134 flows into the flue 150 together with the sample gas in the distal end portion of the second sleeve 134. Thus, it is possible to prevent the sample gas flowing in the flue 150 from flowing into the reflector 131 side.

The second unit 130 is attached to the second attachment portion 160 of the pipe side wall 151 constituting the flue 150.

The second attachment portion 160 includes a first attachment flange 162 disposed at an opening 161 of the pipe side wall 151, for example.

A blocking plate 164 is attached so as to shield the gap 163 between the opening 161 of the second attachment portion 160 and the second sleeve 134.

The blocking plate 164 suppresses the sample gas from flowing into the gap 163 similarly to the blocking plate 119.

In this gas analyzing apparatus 100, the purge gas is supplied to the first sleeve 117 and the second sleeve 134 so that the optical system members of the light emission portion 112, the light receiving portion 113 and the reflector 131 are prevented from being exposed to the sample gas flowing in the flue 150. In addition, it is possible to specify the region to be measured to a region between the distal ends of the first sleeve 117 and the second sleeve 134. In the illustrated example, the distal ends of the first sleeve 117 and the second sleeve 134 are positioned substantially at the same position as the inner surface 156 of the pipe side wall 151.

In order to prevent a part of the sample gas flowing in the flue 150 from flowing into the gap between the first sleeve 117 and the opening 153 as well as in the gap between the second sleeve 134 and the opening 161, the blocking plates 119 and 164 are respectively disposed on the first sleeve 117 and the second sleeve 134.

Thus, temperature distribution of the sample gas on the upstream side and the downstream side becomes uniform, and hence the thermal lens effect phenomenon is reduced so that measurement accuracy can be improved. In addition, optical axis adjustment upon installation can be easily performed in short time.

Fourth Embodiment

Figure 6:
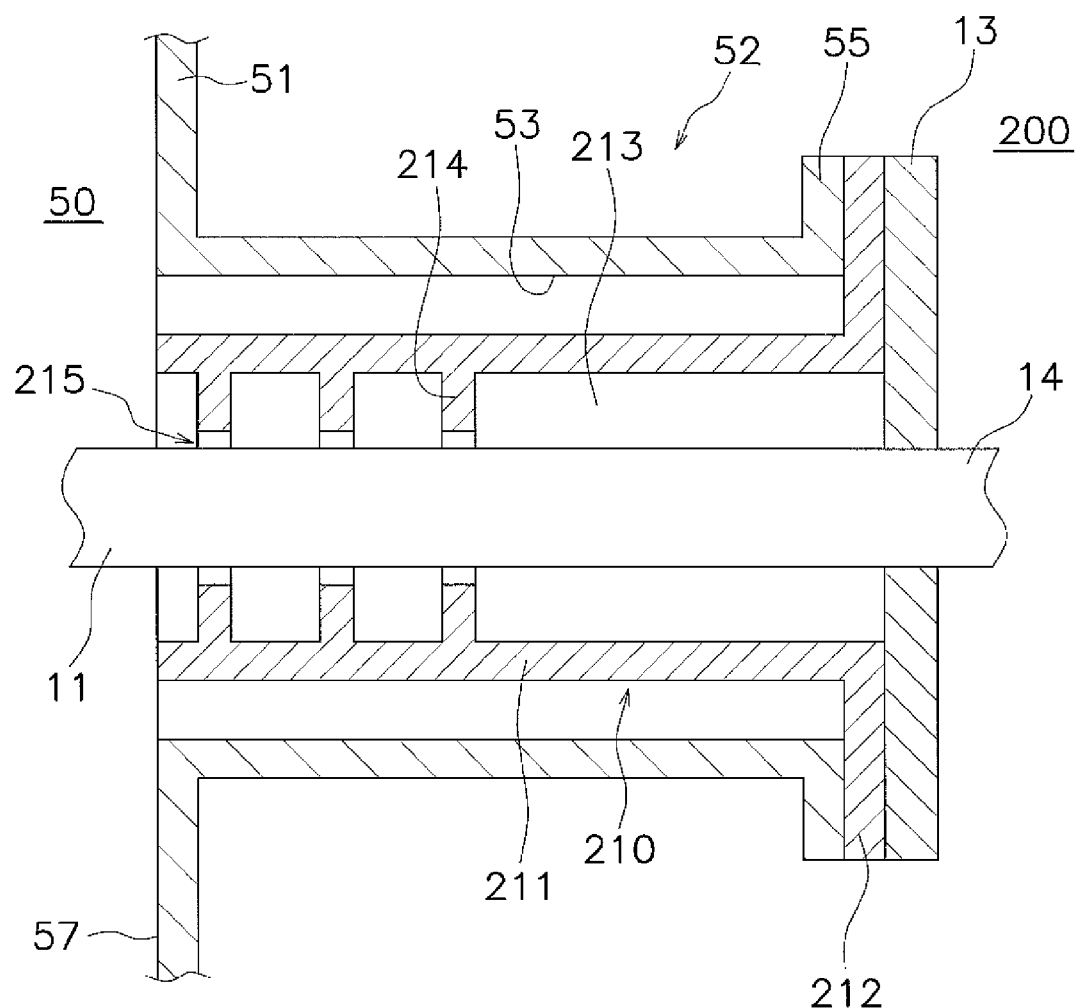
FIG. 6 is a cross-sectional view of a main part of a gas analyzing apparatus of a fourth embodiment

FIG. 6 is a cross-sectional view illustrating a main part of a gas analyzing apparatus 200 according to a fourth embodiment.

In the fourth embodiment, a modification of the previously described structure of the blocking plate and mounting.

The gas analyzing apparatus 200 includes the probe tube 11, the analyzing unit (not shown), the flange 13, and the light guide tube 14, which are the same as those in the first embodiment, and detailed description thereof is omitted.

The pipe side wall 51 is equipped with an attachment flange 55 for fixing the gas analyzing apparatus 200.

An attachment assist member 210 (an example of the attachment assist member) is attached to the attachment flange 55.

The attachment assist member 210 is disposed in the opening 53 of the pipe side wall 51, and includes a tube-like main body portion 211 enclosing a part of the probe tube 11, and a flange portion 212 fixed to the attachment flange 55 by means of welding or screwing.

The main body portion 211 of the attachment assist member 210 has a hollow tube-like shape including an inner circumferential surface forming a gap 213 (an example of the gap) with the outer circumference surface of the probe tube 11.

In addition, the attachment assist member 210 includes blocking plates 214 (an example of the blocking plate) attached to the inner circumferential surface. The blocking plate 214 includes an opening 215 having the middle part through which the probe tube 11 is inserted.

It is preferred that the inner circumference edge of the blocking plate 214 and the outer circumference surface of the probe tube 11 should contact with each other or be close to each other.

The attachment assist member 210 can be designed in advance in accordance with a size of the probe tube 11. Therefore, the inner diameter of the opening 215 can be substantially the same as the outer diameter of the probe tube 11. In this case, the inner circumference edge of the blocking plate 214 and the outer circumference surface of the probe tube 11 contact with each other. Therefore, it is possible to block between the flue 50 and the gap 213 by the blocking plates 214 so that thermal insulation effect can be enhanced.

In other words, it is possible to pre-design the shape and dimensions of the blocking plates 214 provided in the attachment assist member 210 corresponding to the outer diameter of the probe tube 11, regardless of the state of the pipe wall, it is possible to prevent the sample gas to flow into the outer circumferential surface of the probe tube 11 in the pipe side wall. Therefore, the mounting process is easier and it is possible to omit the initial effort.

When the calibration is performed, it is possible to perform the adjustment work by changing an attachment position of the attachment assist member 210 without removing the probe tube 11, and hence the work process can be simplified.

It is preferable that at least one blocking plate 214 is disposed so as to be close to the inner surface 57 of the pipe side wall 51. In the illustrated example, three blocking plates 214 are disposed with spaces in the axis direction of the probe tube 11.

In this fourth embodiment, because the blocking plates 214 are disposed on the main body portion 211 of the attachment assist member 210, it is possible to prevent a part of the sample gas flowing in the flue 50 from flowing into the periphery of the probe tube 11 in the region positioned inside the pipe side wall 51.

Therefore, even if the purge gas is allowed to flow inside the probe tube 11, since temperature around the probe tube 11 positioned inside the pipe side wall 51 is stable, temperature distribution on the light path of the measurement light is stabilized, it is possible to maintain a uniform temperature in the radial cross section of the probe tube, and as a result, and it is thereby possible to prevent a decrease in measurement accuracy due to the thermal lens effect phenomenon.

The blocking plates 214 of the attachment assist member 210 can have the opening 215 corresponding to the outer diameter of the probe tube 11. Therefore, the probe tube 11 can be attached to an arbitrary pipe side wall 51 via the attachment assist member 210 as long as it has the opening 53 having a shape and a size such that the attachment assist member 210 can be inserted in the opening 53.

In the illustrated example, there is a gap between the main body portion 211 of the attachment assist member 210 and the inner circumferential surface of the pipe side wall 51. In this case, a part of the sample gas may flow into between the main body portion 211 of the attachment assist member 210 and the opening 53 of the pipe side wall, but it is possible to suppress heat transmission to the purge gas flowing inside the probe tube 11 by a thermal insulating layer formed by the gap 213 between the attachment assist member 210 and the probe tube 11.

It is possible to attach the above-mentioned attachment assist member including the blocking plate to between the first sleeve 66 and the opening 83 of the pipe side wall 81, as well as between the second sleeve 76 and the opening 93 of the pipe side wall 81 in the second embodiment described above.

In addition, it is possible to attach the above-mentioned attachment assist member including the blocking plate to between the first sleeve 117 and the opening 153 of the pipe side wall 151, as well as between the second sleeve 134 and the opening 161 of the pipe side wall 81 in the third embodiment.

Fifth Embodiment

Figure 7:
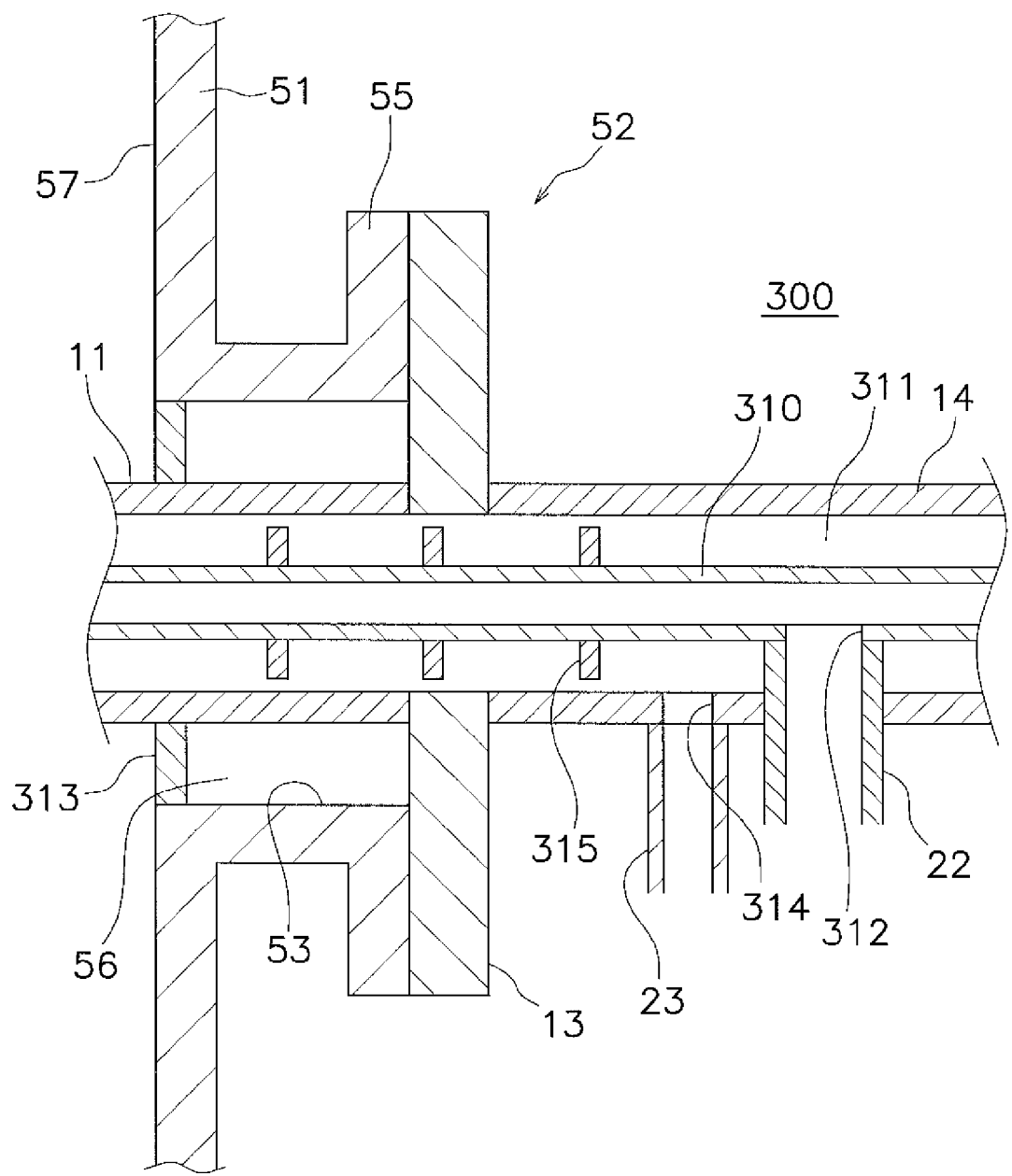
FIG. 7 is a cross-sectional view of a main part of a gas analyzing apparatus of a fifth embodiment.

FIG. 7 is a cross-sectional view illustrating a main part of a gas analyzing apparatus 300 in the fifth embodiment.

The gas analyzing apparatus 300 includes a probe tube 11, an analyzing unit (not shown), a flange 13, and a light guide tube 14, which are the same as those in the first embodiment, and detailed description thereof is omitted.

The pipe side wall 51 includes an attachment flange 55 for fixing the gas analyzing apparatus 300.

The probe tube 11 is attached to the attachment flange 55 via the flange 13.

A purge gas feed tube 310 is disposed on the inner wall surfaces of the probe tube 11 and the light guide tube 14 with a gap 311. A part of the purge gas feed tube 310 disposed inside the probe tube 11 and a part of the same disposed inside the light guide tube 14 may be integrally formed, or the purge gas feed tube 310 may be split into the probe tube 11 side and the light guide tube 14 side at a portion of the flange 13.

The purge gas feed tube 310 has a tube-like shape having a hollow part and is equipped with a connection hole 312 to which the purge gas feed portion 22 is connected. The purge gas supplied from the purge gas feed portion 22 is supplied to the hollow part of the purge gas feed tube 310 via the connection hole 312 and flows toward the distal end portion.

In addition, the hollow part of the purge gas feed tube 310 constitutes a light path, through which the measurement light emitted from the light emission portion (not shown) passes through to the reflector (not shown) side, and the measurement light reflected by the reflector to pass through the measurement region of the probe tube 11 passes through to the light receiving portion (not shown) side.

The purge gas feed tube 310 has substantially the same inner diameter from the connection hole 312 with the purge gas feed portion 22 to the distal end portion positioned at the vicinity of the end portion of the measurement region of the probe tube 11.

It is preferred that the inner diameter of the purge gas feed tube 310 is set so that the purge gas flow becomes a laminar flow in relationship with the flow rate of the purge gas passing through inside of the purge gas feed tube 310, and is set so that Reynolds number becomes smaller than 2300.

The distal end portion of the purge gas feed tube 310 is positioned at one end of the measurement region in the probe tube 11 so that the purge gas collides the sample gas introduced into the probe tube 11 and flows into the flue 50.

Thus, the purge gas introduced into the probe tube 11 via the purge gas feed tube 310 prevents the optical system member from being polluted by the sample gas and defines the measurement region by the optical system member.

The probe tube 11 is equipped with a blocking plate 313 for shielding the gap 56 between the probe tube 11 and the opening 53 of the pipe side wall 51.

The blocking plate 313 is disposed close to the inner surface 57 of the pipe side wall 51 so as to prevent a part of the sample gas passing through inside the flue 50 from flowing into the gap 56 between the probe tube 11 and the opening 53 of the pipe side wall 51.

It is preferred that the outer circumference rim of the blocking plate 313 in the radial direction should contact with the inner circumferential surface of the opening 53, but the effect of preventing the sample gas from flowing into the gap 56 is obtained even if there is a small gap.

In this way, by disposing the blocking plate 313 on the outer surface of the probe tube 310, it is possible to prevent the sample gas from flowing into the periphery of the probe tube 11 positioned inside the pipe side wall 51.

In this fifth embodiment, because the inner hollow of the purge gas feed tube 310 is the light path of the measurement light, temperature gradient on the light path is made continuous by the thermal insulation effect by the gap 311 between the purge gas feed tube 310 and the probe tube 11. Thus, it is possible to prevent occurrence of the thermal lens effect phenomenon due to unevenness of temperature distribution.

In addition, because the blocking plate 313 can prevent the sample gas from flowing into the periphery of the probe tube 11 positioned inside the pipe side wall 51. Therefore, temperature distribution of the purge gas inside the purge gas feed tube 310 can be uniformed so that measurement accuracy by the optical system member can be enhanced.

In a case that a second optical system member such as a reflector is attached to the distal end of the probe tube 11, the purge gas is supplied to the distal end portion in order to protect the second optical system member from the sample gas.

In order to supply the purge gas to the distal end portion of the probe tube 11, it is possible to adopt a structure in which the gap 311 between the probe tube 11 and the purge gas feed tube 310 is used for guiding the purge gas to an end of the measurement region, and an additionally disposed distal end portion purge gas feed tube (not shown) is used for guiding the purge gas to the distal end of the probe tube 11.

In this case, a connection hole 314 connected to the second purge gas feed portion 23 is disposed on the light guide tube 14, and the purge gas supplied from the second purge gas feed portion 23 is guided toward the distal end portion of the probe tube 11 via the gap 311 between the probe tube 11 and the purge gas feed tube 310.

In this case, one or more partition plates 315 can be disposed on the outer surface of the purge gas feed tube 310.

The partition plate 315 can be constituted of a disk-like member having the outer circumference rim forming a predetermined gap with the inner circumferential surface of the probe tube 11. This partition plate 315 divides the gap 311 between the probe tube 11 and the purge gas feed tube 310 into a plurality of hollow portions, which are communicated with each other through the gap between the outer circumference rim of the partition plate 315 and the inner circumferential surface of the probe tube 11.

The flow path of the purge gas supplied from the second purge gas feed portion 23 is rapidly narrowed by the gaps between the partition plates 315 and the probe tube 11 when the purge gas passing through the gap 311 between the probe tube 11 and the purge gas feed tube 310, and the flow path is rapidly widened by the hollow portion, so as to occur a turbulent flow, and the purge gas is stirred so that temperature distribution is uniformed.

Therefore, it is possible to maintain the temperature gradient of the measurement light on the light path to be continuous without affecting the temperature distribution of the purge gas passing through inside the purge gas feed tube 310.

In addition, because the purge gas passing through inside the purge gas feed tube in the distal end portion is stirred in advance so that the temperature distribution is uniformed, the purge gas hardly affects the temperature of the sample gas in the measurement region before reaching the optical system member disposed in the distal end portion of the probe tube 11.

The structure of the blocking plate can be applied also to a case where the purge gas feed tube is disposed on each of the first sleeve 66 and the second sleeve 76 in the second embodiment described above.

In addition, the structure of the blocking plate can be applied also to a case where the purge gas feed tube is disposed on each of the first sleeve 117 and the second sleeve 134 in the third embodiment.

Other Embodiments

Although an embodiment is described above, it is not limited to the embodiment described above and can be modified variously within the scope without deviating from the spirit thereof. In particular, the plurality of embodiments and variation examples described in this specification can be combined arbitrarily as necessary.

For instance, as for a type of the probe, a type of the gas, a position of the blocking plate, the number of the blocking plates, a shape of the blocking plate, a size of the blocking plate, and an attachment structure of the blocking plate, variation examples thereof can be combined.

Sixth Embodiment

Figure 8:
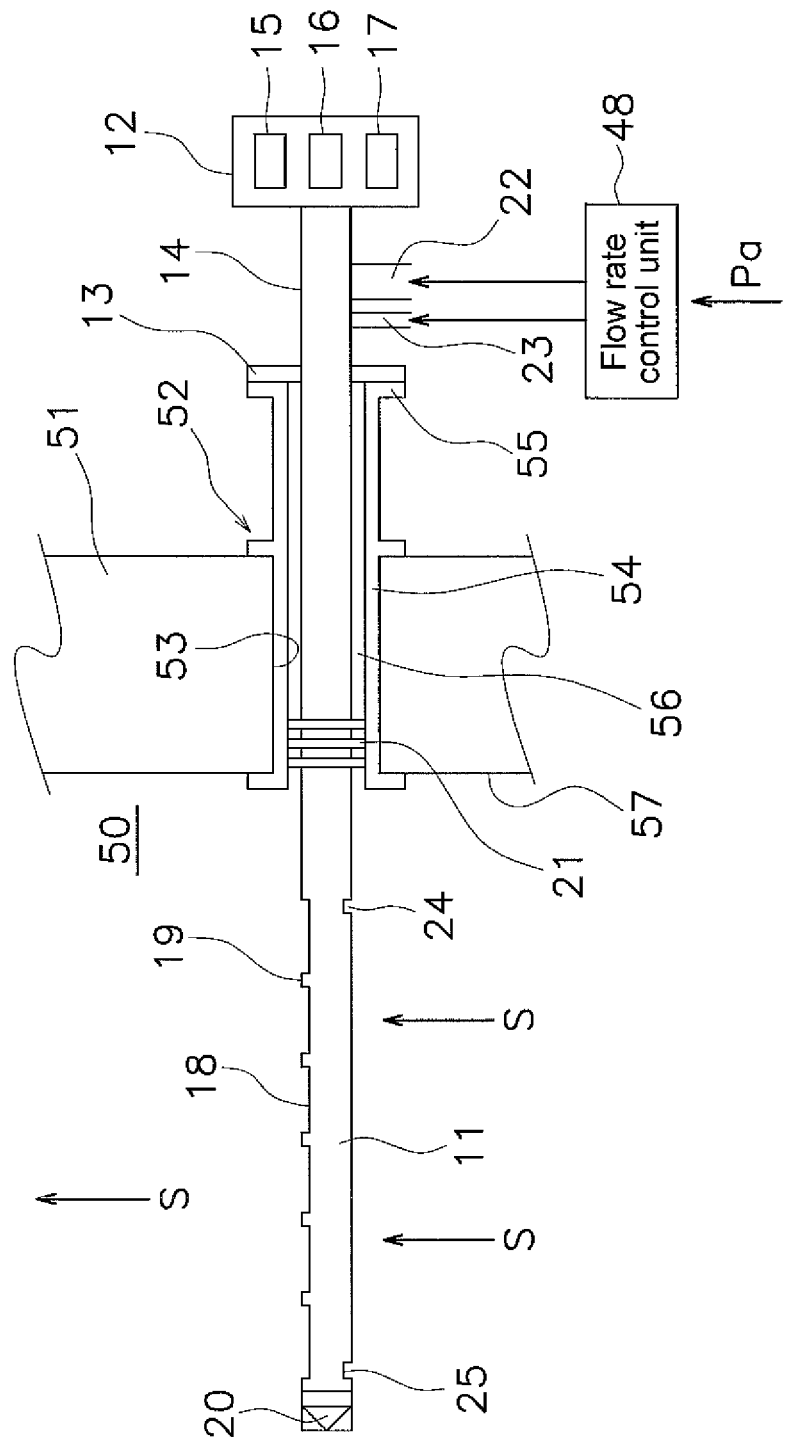
FIG. 8 is a side view of a gas analyzing apparatus of a sixth embodiment.
Figure 9:
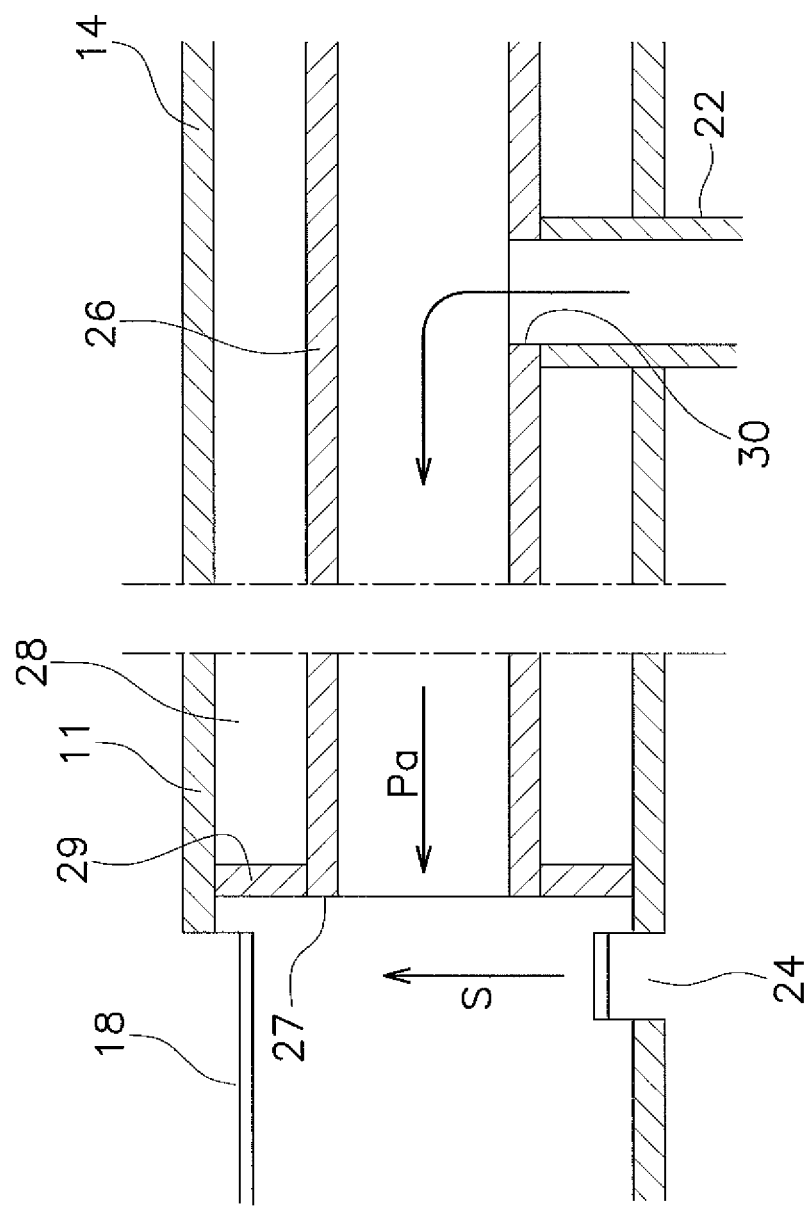
FIG. 9 is an enlarged cross-sectional view of a main part of a gas analyzing apparatus of the sixth embodiment.

FIG. 8 is a side view of a gas analyzing apparatus 1 of a sixth embodiment, and FIG. 9 is an enlarged cross-sectional view of a main part of a gas analyzing apparatus 1 of the sixth embodiment.

The gas analyzing apparatus 1 according to the sixth embodiment includes substantially the same elements of the first embodiment.

Note that in order to feed purge gas Pa to the first purge gas feed portion 22 and the second purge gas feed portion 23, there is disposed a flow rate control unit 48. The flow rate control unit 48 controls pressure by a regulator (not shown), and a needle valve (not shown) is adjusted while checking a flowmeter (not shown) so that the flow rate is controlled.

FIG. 9 is a cross-sectional view at one end of the probe tube 11.

A purge gas feed tube 26 (an example of a purge gas feed tube) is disposed inside the probe tube 11 and the light guide tube 14 with a gap 28 between the purge gas feed tube 26 and each inner wall of the probe tube 11 and the light guide tube 14. The purge gas feed tube 26 may include a part disposed inside the probe tube 11 and a part disposed inside the light guide tube 14 which are integrally formed, or may be separated into the part inside the probe tube 11 and the part disposed inside the light guide tube 14 at the flange 13.

The purge gas feed tube 26 has a tube-like shape having a hollow part with a connection hole 30 to which the first purge gas feed portion 22 is connected. The purge gas supplied from the first purge gas feed portion 22 is fed to the hollow part of the purge gas feed tube 26 via the connection hole 30 and flows in the direction toward a distal end portion 27.

In addition, the hollow part of the purge gas feed tube 26 constitute a light path through which the measurement light emitted from the light emission portion 15 passes toward the reflector 20 and the measurement light reflected by the reflector 20 so as to pass through the measurement region of the probe tube 11 passes toward the light receiving portion 16.

The purge gas feed tube 26 has a substantially uniform inner diameter from the connection hole 30 with the first purge gas feed portion 22 to the distal end portion 27 positioned at a vicinity of the end portion of the measurement region of the probe tube 11.

Since the distal end of the purge gas feed tube 26 is arranged in the vicinity of the end portion of the measurement region, it is possible to prevent the sample gas introduced into the measurement region from flowing toward the optical member, and it is thereby possible to prevent deterioration and contamination of the optical member. In addition, it is possible to prevent uneven temperature distribution in the vicinity of the end portion of the measurement region.

At the distal end portion 27 of the purge gas feed tube 26, there is disposed a blocking plate 29 for blocking the gap 28 between the feed tube 26 and the probe tube 11. Therefore, there is no sample gas that flows into the second gap 28, it is thereby possible to suppress non-uniform temperature distribution of the probe tube 11. In addition, since the second gap 28 is sealed by the second blocking plate 29, a heat insulating effect becomes improved by the second gap 28, and it is thereby possible to prevent the temperature distribution from becoming non-uniform due to the influence of outside air temperature.

On the upstream side of the probe tube 11 disposed on one end portion of the measurement region, there is formed a notch hole 24. The gas flow S flows into the notch hole 24.

As illustrated in FIG. 9, at the distal end portion 27 of the purge gas feed tube 26, the purge gas Pa and the gas flow S collide each other. The purge gas Pa is prevented by the gas flow S from entering the measurement region of the probe tube 11. As a result, measurement error due to the purge gas does not occur in the measurement region. In addition, the gas flow S flowing in through the notch hole 24 is prevented by the purge gas Pa from entering the analyzing unit 12. As a result, it is possible to prevent pollution and corrosion of the optical system such as the light emission portion 15 and the light receiving portion 16. Therefore, it is preferred to set a size of the notch hole 24 larger than inner diameter of the purge gas feed tube 26 so that the gas flow S flowing through the notch hole 24 into the probe tube 11 can cross the entire cross-sectional area of the hollow part of the purge gas feed tube 26.

In this embodiment, the probe tube 11 is attached to the pipe side wall 51 at the flange 13 as a cantilever support. Therefore, the probe tube 11 has a complicated structure at the attachment portion near the flange 13, a joining portion with the first purge gas feed portion 22, and at a joining portion with the analyzing unit 12, and thus an inner diameter thereof may have a variation. Even in such a case, the purge gas can be supplied in a laminar flow state to one end of the measurement region of the probe tube 11 via the purge gas feed tube 26 so that unevenness of temperature distribution can be prevented.

By determining the diameter of the purge gas supply tube 26 while taking into account the flow rate of the purge gas flowing in the interior, it is possible to decrease the Reynolds number, so that it is possible to eliminate non-uniform temperature distribution due to a turbulence in the purge gas. For example, as described above, by using the purge gas feed tube 26 having a uniform inner diameter along the entire length, and further by making the internal purge gas a laminar flow, it is possible to suppress the fluctuation of the measurement light caused by thermal lens effect due to occurrence of heat transferred from the outside, and to increase the measurement accuracy.

Note that the above-mentioned laminar flow state can be securely obtained by flow rate control by the flow rate control unit 48.

In addition, because the gap 28 between the probe tube 11 and the purge gas feed tube 26 is sealed by the blocking plate 29, a thermal insulation effect of the gap 28 can prevent occurrence of unevenness of temperature distribution, due to an influence of outside air temperature, in the purge gas passing through the purge gas feed tube 26.

Note that the purge gas supplied from the second purge gas feed portion 23 is fed to the distal end portion of the probe tube 11 through the purge gas feed tube (not shown) disposed inside the light guide tube 14 and the probe tube 11 and is led into the flue 50 together with the gas flow S flowing through the notch hole 25 of the probe tube 11 into the downstream side. In this way, it is possible to prevent the purge gas from flowing into the measurement region side in the probe tube 11, so that a measurement error due to the purge gas does not occur in the measurement region. In addition, it is possible to prevent the gas flow S flowing in through the notch hole 25 from flowing into the reflector 20 side by the purge gas supplied from the second purge gas feed portion 23, so that pollution and corrosion of the reflector 20 can be prevented.

In this case too, by setting a size of the notch hole 25 larger than a diameter of the purge gas feed tube, it is possible to prevent the purge gas flowing in through the purge gas feed tube from entering the measurement region.

As illustrated in FIG. 8, the blocking plate 21 is disposed on the probe tube 11, so that a part of the gas flow S does not enter the gap 56 between the installation pipe 54 and the probe tube 11. Thus, the effect of preventing unevenness of temperature distribution is further enhanced. However, in this embodiment, the blocking plate 21 is not indispensable.

As long as the shape of the purge gas feed tube 26 is one having a hollow portion through which the measurement light can pass, a cross section thereof can be a polygonal shape, an elliptical shape, or a combination shape thereof.

According to this apparatus, since the purge gas feed tube 26 is located with the second gap 28 between it and the inner surface of the probe tube 11, it is possible to insulate the purge gas passing through the purge gas feed tube 26 from outside air. In addition, even if it is such that its inner diameter is not uniform because the probe tube 11 has a flange joining portion to be attached to the pipe side wall, a pipe side wall joining portion to introduce the purge gas, and an optical element joining portion, by using a purge gas feed tube 26 having an inner diameter smooth without steps with respect to the optical axis direction, it is possible to make a turbulent flow in the purge gas, thereby suppressing the occurrence of the thermal lens effect. The inner diameter of the purge gas feed tube 26 can be used as, for example, having a uniform inner diameter along the entire length. As a result, it is possible to improve the measurement accuracy of the gas analysis processing by the optical system member is no fluctuation of the measuring light. In addition, it is possible to quickly and easily set and adjust the optical axis at the time of the initial installation.

Seventh Embodiment

Figure 10:
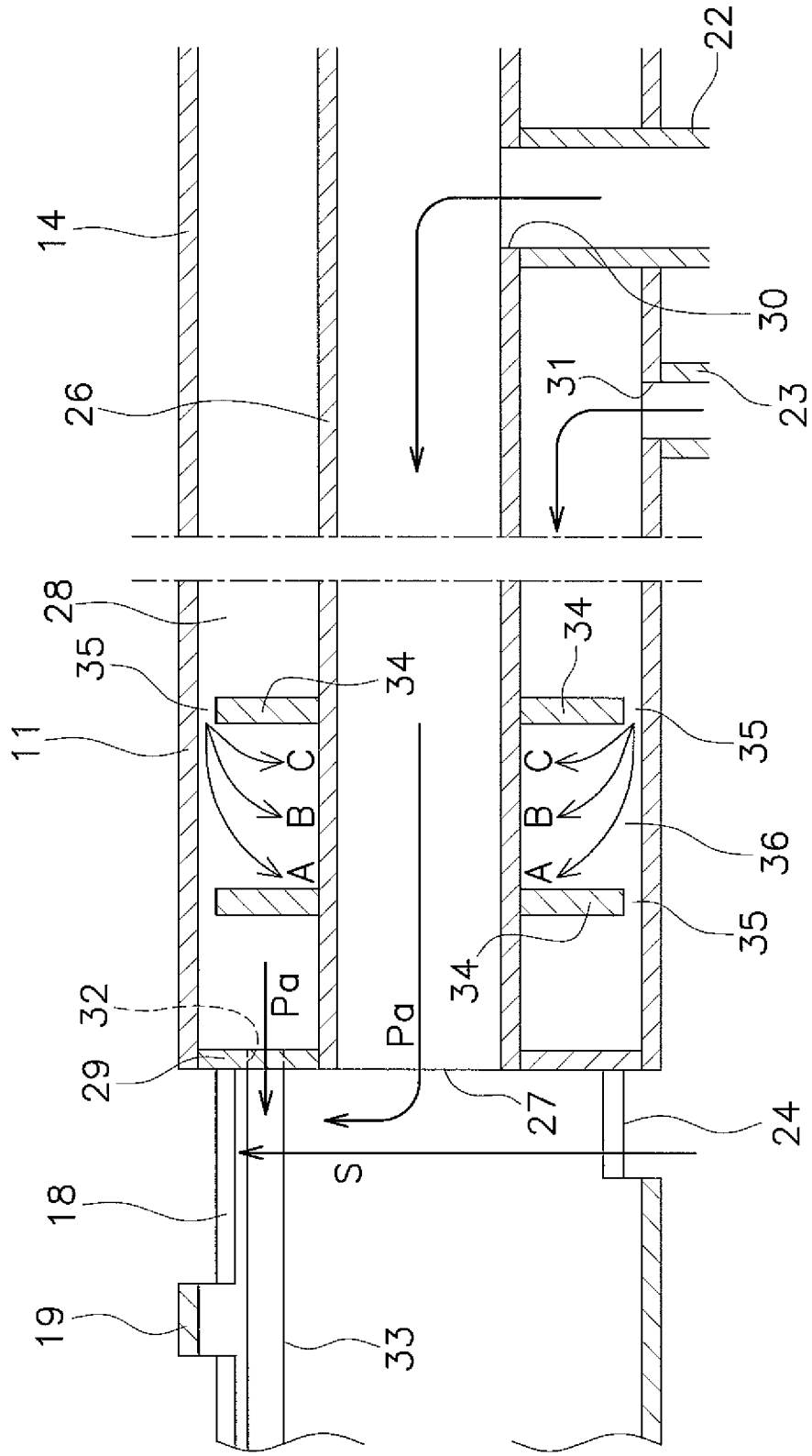
FIG. 10 is an enlarged cross-sectional view of a main part of a gas analyzing apparatus of a seventh embodiment.
Figure 11:
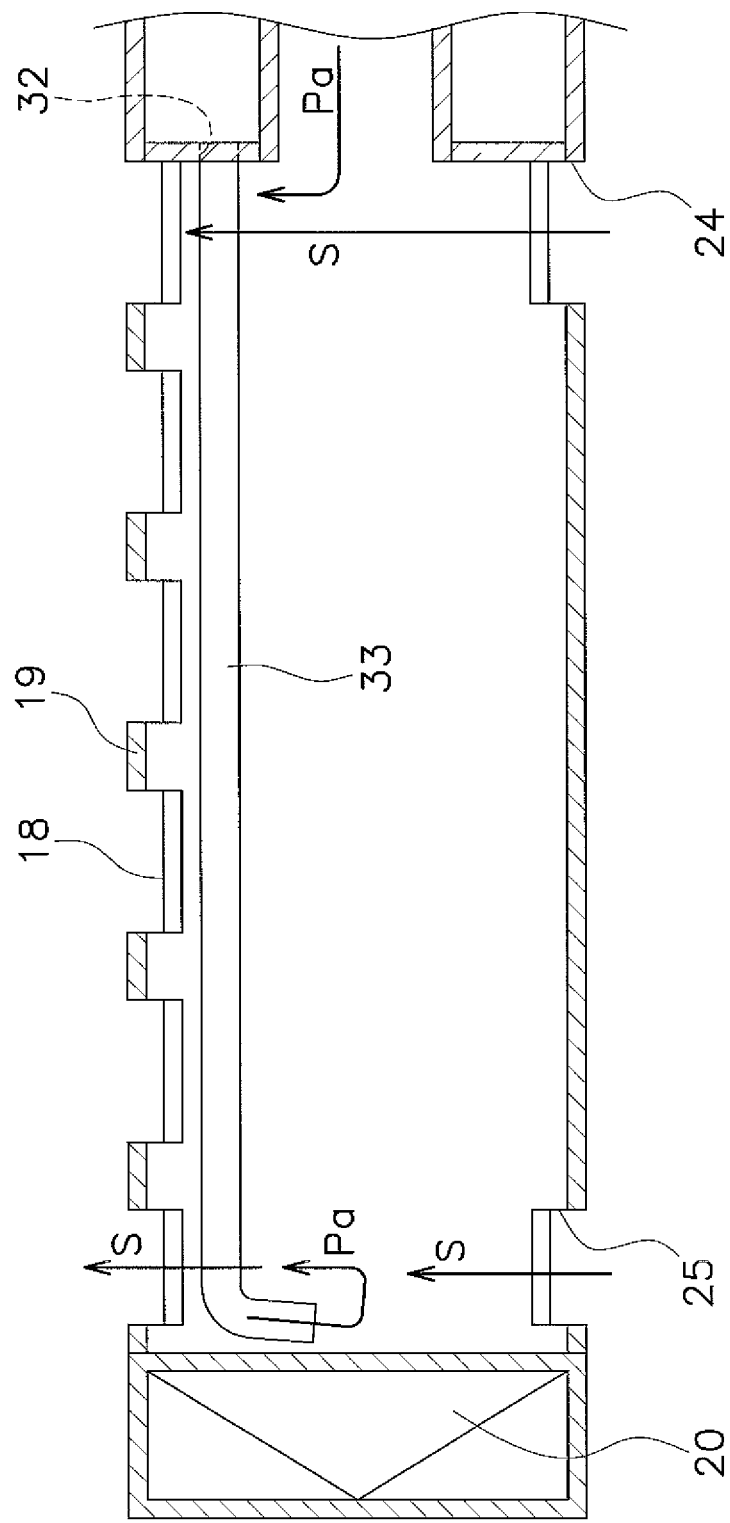
FIG. 11 is an enlarged cross-sectional view of a main part of a gas analyzing apparatus of the seventh embodiment.

FIGS. 10 and 11 are cross-sectional views of a main part of a gas analyzing apparatus according to a seventh embodiment of the present invention.

In the seventh embodiment, the same elements as in the sixth embodiment are denoted by the same numerals, and detailed descriptions thereof are omitted.

Similarly to the sixth embodiment, the gas analyzing apparatus 1 in the seventh embodiment includes a probe tube 11, an analyzing unit (not shown), a flange (not shown), and a light guide tube 14. The light emission portion and the light receiving portion attached to the analyzing unit emits and receives the measurement light so as to perform concentration analysis of the sample gas.

In the hollow part of the probe tube 11, there is disposed a purge gas feed tube 26 with a gap between the purge gas feed tube 26 and the inner surface of the probe tube 11.

The purge gas feed tube 26 has a tube-like shape having a hollow part and has the connection hole 30 formed for connecting to the first purge gas feed portion 22. The purge gas supplied from the first purge gas feed portion 22 is fed to the hollow part of the purge gas feed tube 26 via the connection hole 30, and flows toward a distal end portion 27.

The probe tube 11 has a connection hole 31 to which the second purge gas feed portion 23 is connected. By connecting the second purge gas feed portion 23 to this connection hole 31, the purge gas supplied from the second purge gas feed portion 23 can be led to the gap 28 between the probe tube 11 and the purge gas feed tube 26.

In the distal end portion 27 of the purge gas feed tube 26, there is disposed a blocking plate 29 for blocking the gap 28 between the purge gas feed tube 26 and the probe tube 11, and an opening 32 is formed in the blocking plate 29. The opening 32 of the blocking plate 29 is connected to a distal end portion purge gas feed tube 33 (an example of a distal end portion purge gas feed tube) for supplying the purge gas to a vicinity of the reflector 20 disposed at the distal end of the probe tube 11.

On the upstream sides disposed on both ends of the measurement region of the probe tube 11, there are disposed the notch holes 24 and 25. The gas flow S flows in through the notch holes 24 and 25.

As illustrated in FIG. 10, on the distal end portion 27 of the purge gas feed tube 26, the purge gas Pa and the gas flow S collide each other. The purge gas Pa is prevented from entering the measurement region side in the probe tube 11 by the gas flow S. As a result, a measurement error due to the purge gas does not occur in the measurement region. In addition, the gas flow S is prevented from entering the analyzing unit 12 side by the purge gas Pa. As a result, pollution and corrosion of the optical system such as the light emission portion 15 or the light receiving portion 16 can be prevented.

As illustrated in FIG. 11, in a vicinity of the notch hole 25 and the distal end portion of the distal end portion purge gas feed tube 33, the purge gas Pa and the gas flow S collide each other. The purge gas Pa supplied from the distal end portion purge gas feed tube 33 to the distal end portion of the probe tube 11 flows in the probe tube 11 through the notch hole 25 of the probe tube 11 and is led into the flue 50 together with the gas flow S flowing in the downstream side. In this way, it is possible to prevent the purge gas Pa from entering the measurement region side in the probe tube 11 so that a measurement error due to the purge gas Pa does not occur in the measurement region. In addition, the gas flow S is prevented from entering the reflector 20 side by the purge gas Pa. As a result, it is possible to prevent pollution and corrosion of the reflector 20.

In this way, an opening 32 of the blocking plate 29 and the distal end portion purge gas feed tube 33 are disposed at positions shifted from the middle portion of the probe tube 11 so as not to prevent the flow path of the sample gas entering through the notch holes 24 and 25. As illustrated in the diagram, because the distal end portion purge gas feed tube 33 is disposed on the downstream side of the gas flow S in the probe tube 11, it is possible to prevent the gas flow entering through the notch holes 24 and 25 from colliding the distal end portion purge gas feed tube 33 and from causing convection. It is preferred that the distal end portion of the distal end portion purge gas feed tube 33 is disposed on the upstream side of the gas flow or in the center of the reflector so as to feed the purge gas to the surface of the reflector 20 on the light path of the measurement light.

In the gap 28 between the probe tube 11 and the purge gas feed tube 26, there are disposed a plurality of partition plates 34 (an example of a partition plate) on the outer surface of the purge gas feed tube 26.

If the probe tube 11 has a cylindrical shape, the partition plate 34 is constituted of a disk having a diameter smaller than the inner diameter of the probe tube 11 so that there is a predetermined space 35 between the partition plate 34 and the inner wall surface of the probe tube 11. Thus, the gap 28 between the probe tube 11 and the purge gas feed tube 26 includes a plurality of ring-like hollow portions 36 (an example of the agitation portion) defined by the partition plates 34 and communicated via the spaces 35. Note that the partition plate 34 is not limited to have a disk shape but should have a structure for partitioning the second gap 28 into the plurality of hollow portions 36 so that the hollow portions 36 are communicated via the spaces 35. The shape of the partition plate 34 can be modified appropriately in accordance with the shape of the inner wall surface of the probe tube 11 and the shape of the purge gas feed tube 26.

The purge gas supplied from the second purge gas feed portion 23 flows into the second gap 28 through the connection hole 31, and flows into the distal end portion purge gas feed tube 33 via the opening 32 in the distal end portion 27 of the purge gas feed tube 26.

The purge gas flowing in the second gap 28 passes through the space 35 at a position of the partition plate 34 so that the flow path is narrowed, and the flow path is rapidly expanded in the hollow portion 36. Therefore, a turbulent flow is formed as illustrated by arrows A, B, and C in FIG. 10.

Therefore, the purge gas flowing in the second gap 28 is stirred in the hollow portion 36, and hence the air flow passing through along the inner wall surface of the probe tube 11 that is the outer circumference of the second gap 28 and the air flow passing through along the outer wall surface of the purge gas feed tube 26 are mixed with each other.

In this way, the purge gas supplied to the distal end portion purge gas feed tube 33 passes through the second gap 28 so that the temperature distribution becomes uniform. Therefore, a temperature difference between the purge gas passing through the distal end portion purge gas feed tube 33 disposed in the measurement region and the sample gas led into the probe tube 11 is decreased. In other words, temperature distribution in the probe tube 11 becomes uniform, and as a result, occurrence of the thermal lens effect phenomenon can be prevented.

In summary, the second gap 28 constitutes a second purge gas flow path for feeding a purge gas to the space between the optical member and the measurement region. The hollow portion 36 is provided in the second gap 28, in order to stir the purge gas passing through the second purge gas flow path.

In this case, since the purge gas supplied to one end of the measurement region through the distal end portion purge gas feed tube 33 passes through the second gap 28, the inside of the distal end portion purge gas feed tube 33 is insulated, i.e., it is hardly affected by the outside temperature. In addition, since the temperature distribution of the purge gas passing through the second gap 28 is uniform because it is stirred by the hollow portions 36, the conduction of heat to the distal end portion purge gas feed tube 33 will be uniform, so that the temperature of the purge gas in the optical path of the measurement light is maintained uniform, and it is thereby possible to further suppress the thermal lens effect phenomenon.

As described above, the gas analyzing apparatus comprises a probe tube 11, a light-emitting portion, a light-receiving portion, and a reflector 20. The probe tube 11 is disposed so as to intersect the flow path of the sample gas in the pipe in order to introduce the sample gas into the measurement region in the internal hollow portion. The light-emitting portion emits measurement light into the light measurement region. The light-receiving portion receives the measurement light passed through the sample gas in the measurement region. The reflector 20 reflects the light emitted from the light-emitting portion to the light-receiving portion. The apparatus further comprises a distal end portion purge gas feed tube 33.

The distal end portion purge gas feed tube 33 is communicated with the second gap 28, and its tip is located in the vicinity of the reflector 20. Then, the purge gas is supplied to the vicinity of the reflector 20 through the second purge gas flow including the second gap 28 and the distal end portion purge gas feed tube 33.

In this case, since the purge gas supplied to one end of the measurement region through the distal end portion purge gas feed tube 33 passes through the second gap 28, the inside of the distal end portion purge gas feed tube 33 is insulated, i.e., it is hardly affected by the outside temperature. In addition, since the temperature distribution of the purge gas passing through the second gap 28 is uniform because it is stirred by the hollow portions 36, the conduction of heat to the distal end portion purge gas feed tube 33 will be uniform, so that the temperature of the purge gas in the optical path of the measurement light is maintained uniform, and it is thereby possible to further suppress the thermal lens effect phenomenon.

Eighth Embodiment

Figure 12:
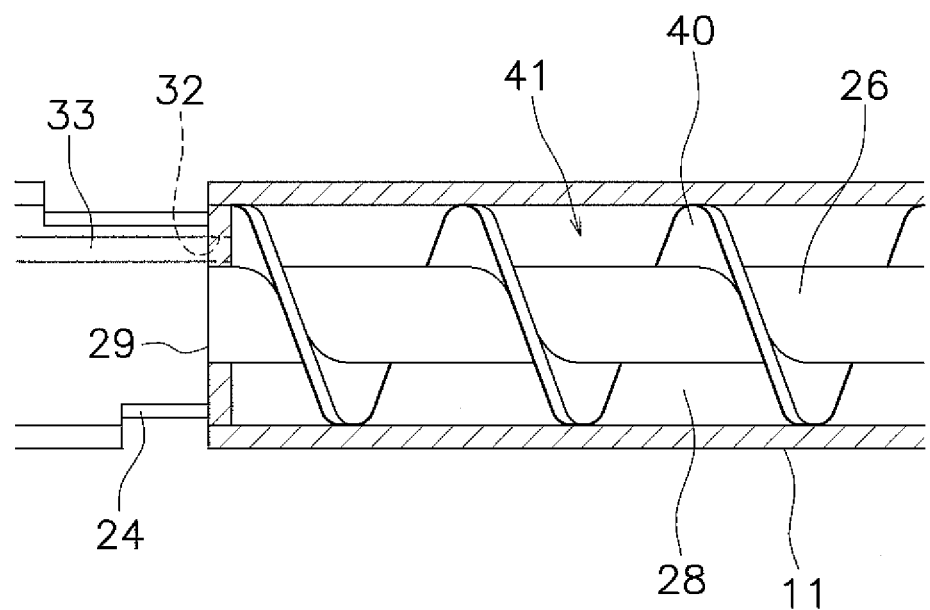
FIG. 12 is an enlarged cross-sectional view of a main part of a gas analyzing apparatus of an eighth embodiment.

FIG. 12 is an enlarged perspective view of a main part of a gas analyzing apparatus of an eighth embodiment.

In the eighth embodiment, a modification of the agitation portion is described.

In the eighth embodiment, the same elements as in the sixth and the seventh embodiments are denoted by the same numerals, and hence detailed descriptions thereof are omitted.

Similarly to the sixth embodiment, the gas analyzing apparatus 1 in the eighth embodiment includes a probe tube 11, an analyzing unit (not shown), a flange (not shown), and a light guide tube (not shown). The measurement light is emitted and received by the light emission portion and the light receiving portion attached to the analyzing unit so that the concentration analysis of the sample gas is performed.

In the hollow part of the probe tube 11, there is disposed a purge gas feed tube 26 with a gap 28 between the purge gas feed tube 26 and the inner surface of the probe tube 11.

The purge gas feed tube 26 has a tube-like shape having a hollow part, and the purge gas supplied to the hollow part from the first purge gas feed portion (not shown) is guided to the distal end portion 27.

A second purge gas feed portion (not shown) is connected to the probe tube 11, and the purge gas supplied from the second purge gas feed portion is guided into the gap 28 between the probe tube 11 and the purge gas feed tube 26.

At the distal end portion 27 of the purge gas feed tube 26, there is disposed a blocking plate 29 for blocking the gap 28 between the purge gas feed tube 26 and the probe tube 11. The blocking plate 29 is formed with an opening 32, and the distal end portion purge gas feed tube 33 for guiding the purge gas to the distal end side of the probe tube 11 is connected to the opening 32.

In this case too, as illustrated in the diagram, the distal end portion purge gas feed tube 33 is disposed on the downstream side of the gas flow S in the probe tube 11. Thus, it is possible to prevent the gas flow led in through the notch hole 24 from colliding the distal end portion purge gas feed tube 33 and from causing convection.

On the outer wall surface of the purge gas feed tube 26, there is formed a helical protrusion 40 (an example of the partition plate). An outer rim of the protrusion 40 may contact with the inner wall surface of the probe tube 11, or a gap may be formed between the outer rim and the inner wall surface of the probe tube 11. By this protrusion 40, there is formed a helical gas flowing path 41 (an example of the agitation portion) turning around the outer wall surface of the purge gas feed tube 26 in the gap 28 between the probe tube 11 and the purge gas feed tube 26.

The purge gas supplied from the second purge gas feed portion is introduced into the gap 28 between the probe tube 11 and the purge gas feed tube 26 and flows toward the opening 32. In this case, the purge gas flows in a helical manner along the protrusion 40 formed on the outer wall surface of the purge gas feed tube 26, and reaches the opening 32 while being stirred in the gas flowing path 41.

In this way, the purge gas supplied to the distal end portion purge gas feed tube 33 passes through the gap 28 so as to have uniform temperature distribution. Therefore, a temperature difference between the purge gas passing through the distal end portion purge gas feed tube 33 disposed in the measurement region and the sample gas introduced into the probe tube 11 is decreased, and hence temperature distribution in the probe tube 11 becomes uniform so that occurrence of the thermal lens effect phenomenon can be prevented.

Ninth Embodiment

Figure 13:
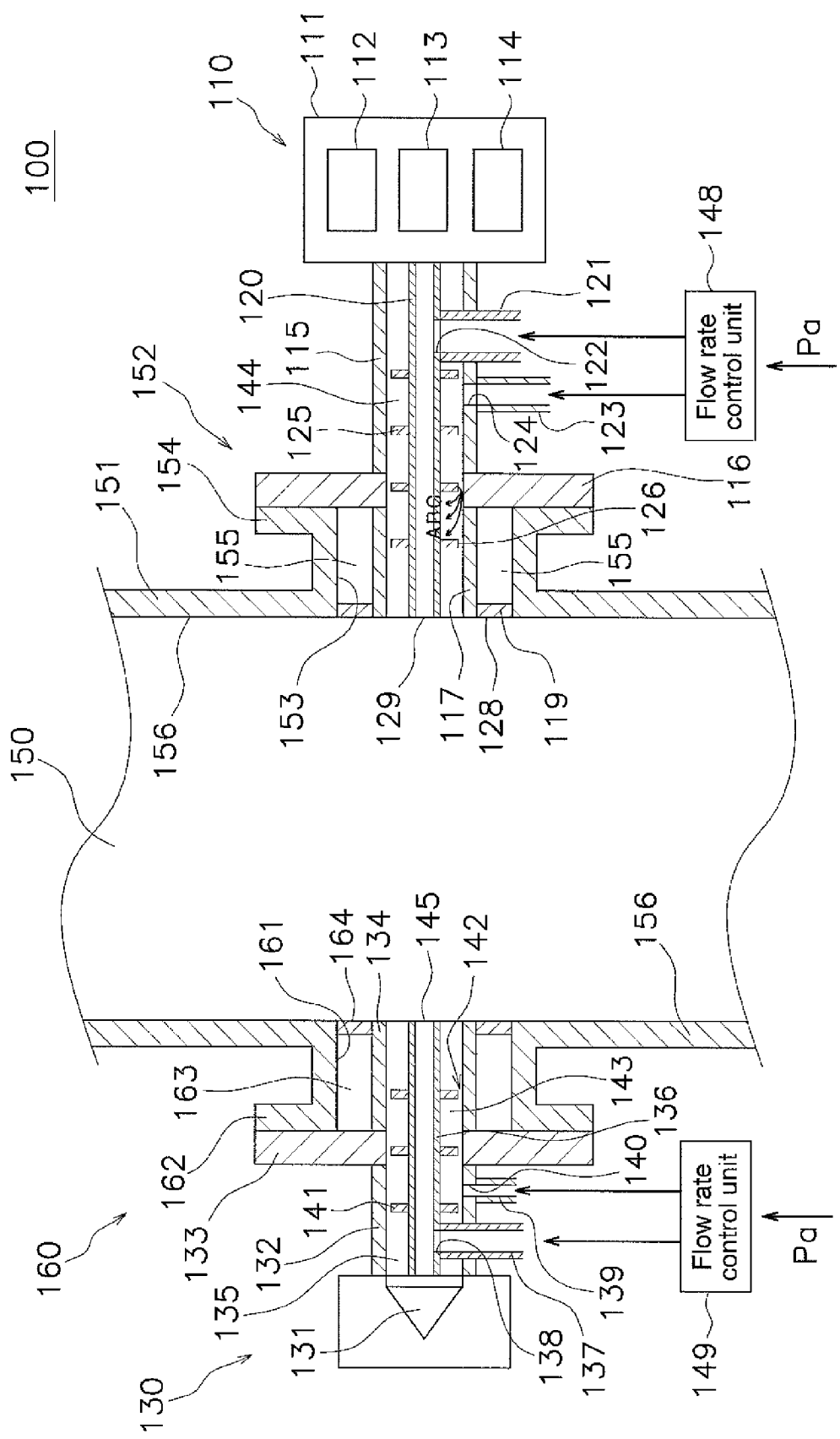
FIG. 13 is a perspective view of a main part of a gas analyzing apparatus of a ninth embodiment.
Figure 14:
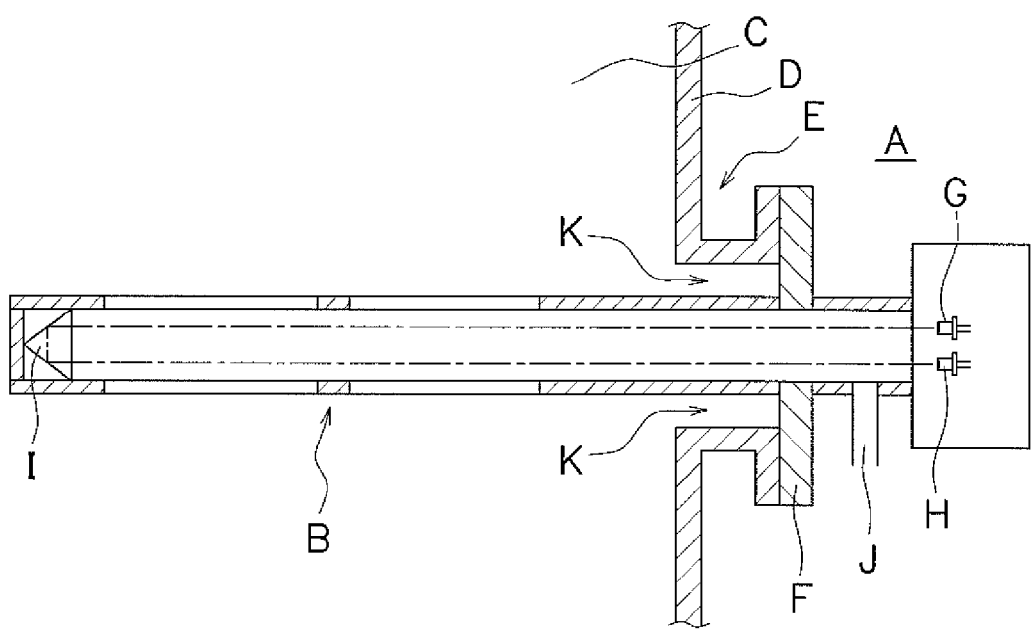
FIG. 14 is an explanatory diagram of a main part of a gas analyzing apparatus of a conventional example.

FIG. 13 is a side cross-sectional view of a gas analyzing apparatus 100 according to a ninth embodiment.

The gas analyzing apparatus 100 includes a first unit 110 and a second unit 130 disposed at opposed positions with respect to a pipe side wall 151.

The first unit 110 includes an analyzing unit 111, a first light guide tube 115, a first flange 116, and a first sleeve 117 (an example of the tube-like member).

The analyzing unit 111 includes a light emission portion 112, a light receiving portion 113, and a control unit 114.

The light emission portion 112 is a light source emitting a laser beam to be the measurement light through the first light guide tube 115 and the first sleeve 117 to the gas to be measured. The light emission portion 112 can be constituted of an infrared laser generation apparatus for emitting light in a predetermined wavelength band having high straightness.

The light receiving portion 113 is a light receiving element that receives the measurement light entering through the gas to be measured in the flue.

The control unit 114 controls the laser beam emission from the light emission portion 112 and analyzes components of the gas to be measured based on the measurement light received by the light receiving portion 113.

The analyzing unit 111 is connected to the first sleeve 117 via the first light guide tube 115 and the first flange 116.

Inside the first light guide tube 115 and the first sleeve 117 of the first unit 110, there is disposed a first purge gas feed tube 120 via a second gap 144. A part of the first purge gas feed tube 120 disposed inside the first sleeve 117 and a part of the first purge gas feed tube 120 disposed inside the first light guide tube 115 may be formed integrally, or the first sleeve 117 side and the first light guide tube 115 side may be separated at a portion of the first flange 116.

The first purge gas feed tube 120 has a tube-like shape including a hollow part, and is provided with a connection hole 122 to which a first purge gas feed portion 121 is connected. The purge gas supplied from the first purge gas feed portion 121 is supplied to the hollow part of the first purge gas feed tube 120 via the connection hole 122, and flows in the direction to the distal end portion.

In this way, the hollow part of the first purge gas feed tube 120 provides a path guiding the purge gas supplied from the first purge gas feed portion 121, and provides a path of the measurement light emitted from the light emission portion 112.

The first purge gas feed tube 120 has a substantially uniform inner diameter from the connection hole 122 to a distal end portion 129 positioned at the vicinity of the inner circumferential surface of the pipe side wall 151.

Thus, the purge gas passing through the hollow part of the first purge gas feed tube 120 can be made a laminar flow, and occurrence of the thermal lens effect phenomenon due to uneven temperature distribution can be prevented.

The first light guide tube 115 is formed with a connection hole 124 to which a second purge gas feed portion 123 is connected. By connecting the second purge gas feed portion 123 to this connection hole 124, the purge gas supplied from the second purge gas feed portion 123 can be introduced into the second gap 144 between the first sleeve 117 and the first purge gas feed tube 120.

Note that there is disposed a flow rate control unit 148 in order to supply the purge gas Pa to the first purge gas feed portion 121 and the second purge gas feed portion 123. The flow rate control unit 148 controls the pressure by a regulator (not shown), and a flow rate is controlled by adjusting a needle valve (not shown) while viewing the flowmeter (not shown).

In the second gap 144 between the first sleeve 117 and the first purge gas feed tube 120, a plurality of partition plates 125 (an example of the partition plate) are disposed on the outer surface of the first purge gas feed tube 120.

In a case where the first sleeve 117 has a cylindrical shape, the partition plate 125 is constituted of a disk having a smaller diameter than the inner diameter of the first sleeve 117 so that a predetermined space 126 is formed between the partition plate 125 and the inner wall surface of the first sleeve 117. Thus, the second gap 144 between the first sleeve 117 and the first purge gas feed tube 120 has a structure in which a plurality of ring-like hollow portions 127 (an example of the stifling portion) defined by the partition plates 125 are communicated through the space 126. Note that the shape of the partition plate 125 is not limited to the disk shape but can be variously modified in accordance with a shape of the inner wall surface of the first sleeve 117 and a shape of the first purge gas feed tube 120, as long as it constitutes a structure in which the second gap 144 is partitioned into the plurality of hollow portions 127, and the hollow portions 127 are communicated through the space 126.

The purge gas supplied from the second purge gas feed portion 123 flows into the second gap 144 thorough the connection hole 124, and is guided into a flue 150 through the plurality of hollow portions 127.

The purge gas flowing in the second gap 144 passes through the space 126 in a position of the partition plate 125 so that the flow path is narrowed, and the flow path is rapidly expanded in the hollow portion 127. Therefore, a turbulent flow is formed as illustrated by arrows A, B, and C in FIG. 7.

Therefore, since the purge gas flowing in the second gap 144 is stirred in the hollow portion 127, the air flow passing through along the inner wall surface of the first sleeve 117 and the air flow passing through along the outer wall surface of the first purge gas feed tube 120 are mixed with each other.

In this way, the temperature distribution of the purge gas flowing in the second gap 144 becomes uniform. Thus, it is possible to prevent the purge gas flowing in the first purge gas feed tube 120 from being affected by uneven temperature of the outside air, and it is thereby possible to make the temperature distribution uniform on the light path of the measurement light. As a result, occurrence of the thermal lens effect phenomenon can be prevented, and the measurement accuracy can be enhanced.

In the example illustrated in FIG. 13, the second gap 144 between the first sleeve 117 and the first purge gas feed tube 120 is opened toward the flue 150 at the distal end portion, but it is possible to dispose a blocking plate to the distal end portion. In this case, since an opening is formed in the blocking plate so as to be disposed on the upstream side of the gas flow S than the distal end portion of the first purge gas feed tube 120, it is possible to effectively flow the purge gas that prevents the sample gas from reaching the optical system member.

In addition, by disposing this blocking plate to the distal end portion 129 of the first purge gas feed tube 120, the distal end portion 129 of the first purge gas feed tube 120 can be fixed to the first sleeve 117. Thus, it is possible to prevent the distal end portion 129 of the first purge gas feed tube 120 from being vibrated, thereby enhancing the measurement accuracy.

A first attachment portion 152 includes a first attachment flange 154 that is disposed on an opening 153 of the pipe side wall 151, for example.

A blocking plate 128 is attached so as to shield a gap 155 between the opening 153 of the first attachment portion 152 and the first sleeve 117.

The blocking plate 128 is disposed in a vicinity of an inner surface 156 of the pipe side wall 151. In this way, since the blocking plate 128 is disposed on the flue 150 side, it is possible to prevent the sample gas from flowing into the gap 155.

The blocking plate 128 is a disk-like member fixed to the outer circumference surface of the first sleeve 117, and the outer circumference rim is close to or contacts with an inner circumferential surface of the opening 153. In the former close case, it is preferred that the gap should be small from viewpoint of shielding the sample gas. In addition, in the latter contacting case, the gap 155 is shielded so that the effect of blocking the sample gas is enhanced.

The illustrated example shows an example where a single blocking plate 119 is attached to the first sleeve 117, but it is possible to dispose a plurality of blocking plates with a space between each other in an axis direction of the first sleeve 117. In this case, it is harder for the sample gas to flow into the gap 155. In this embodiment, the blocking plate 119 is not indispensable.

The second unit 130 includes a reflector 131, a second light guide tube 132, a second flange 133, a second sleeve 134 (an example of the tube-like member).

The reflector 131 reflects the measurement light emitted from the light emission portion 112 to the light receiving portion 113 side, and can be constituted of a corner-cube prism.

The reflector 131 is connected to the second sleeve 134 via the second light guide tube 132 and the second flange 133.

A second purge gas feed tube 136 is disposed inside the second light guide tube 132 and the second sleeve 134 of the second unit 130 with a second gap 135 between it and the second light guide tube 132 as well as the second sleeve 134. A part of the second purge gas feed tube 136 disposed inside the second sleeve 134 and a part of the same disposed inside the second light guide tube 132 may be formed integrally, or the second sleeve 134 side and the second light guide tube 132 side of the second purge gas feed tube 136 may be separated at a portion of the second flange 133.

The second purge gas feed tube 136 has a tube-like shape including a hollow part, and is provided with a connection hole 138 to which a third purge gas feed portion 137 is connected. The purge gas supplied from the third purge gas feed portion 137 is supplied to the hollow part of the second purge gas feed tube 136 via the connection hole 138, and flows toward the distal end portion.

In this way, the hollow part of the second purge gas feed tube 136 provides a path guiding the purge gas supplied from the third purge gas feed portion 137, and provides a path of the measurement light emitted from the light emission portion 112 and reflected by the reflector 131.

The second purge gas feed tube 136 has a substantially uniform inner diameter from the connection hole 138 to a distal end portion 145 positioned at the vicinity of the inner circumferential surface of the pipe side wall 151.

Thus, since the purge gas passing through the hollow part of the second purge gas feed tube 136 can be a laminar flow, occurrence of the thermal lens effect phenomenon due to uneven temperature distribution can be prevented.

The second light guide tube 132 is formed with a connection hole 140 to which a fourth purge gas feed portion 139 is connected. The fourth purge gas feed portion 139 is connected to this connection hole 140, so that the purge gas supplied from the fourth purge gas feed portion 139 can be introduced to the second gap 135 between the second sleeve 134 and the second purge gas feed tube 136.

Note that there is disposed a flow rate control unit 149 in order to supply the purge gas Pa to the third purge gas feed portion 137 and the fourth purge gas feed portion 139. The flow rate control unit 149 controls the pressure by a regulator (not shown), and a flow rate is controlled by adjusting a needle valve (not shown) while viewing the flowmeter (not shown).

In the second gap 135 between the second sleeve 134 and the second purge gas feed tube 136, a plurality of partition plates 141 are disposed on the outer surface of the second purge gas feed tube 136.

In a case where the second sleeve 134 has a cylindrical shape, the partition plate 141 is constituted of a disk having a smaller diameter than the inner diameter of the second sleeve 134 so that a predetermined space 142 is formed between the partition plate 141 and the inner wall surface of the second sleeve 134. Thus, the gap 135 between the second sleeve 134 and the second purge gas feed tube 136 has a structure in which a plurality of ring-like hollow portions 143 defined by the partition plates 141 are communicated through the spaces 142. Note that the shape of the partition plate 141 is not limited to the disk shape but can be variously modified in accordance with a shape of the inner wall surface of the second sleeve 134 and a shape of the second purge gas feed tube 136, as long as it constitutes a structure in which the gap 135 is partitioned into the plurality of hollow portions 143, and the hollow portions 143 are communicated through the spaces 142.

The purge gas supplied from the fourth purge gas feed portion 139 flows into the gap 135 thorough the connection hole 140 and is guided into the flue 150 through the plurality of hollow portion 143.

The purge gas flowing in the gap 135 passes through the space 142 in a position of the partition plate 141 so that the flow path is narrowed, and the flow path is rapidly expanded in the hollow portion 143. Therefore, a turbulent flow is formed similarly to the first sleeve 117 side.

Therefore, since the purge gas flowing in the gap 135 is stirred in the hollow portion 143, the air flow passing through along the inner wall surface of the second sleeve 134 and the air flow passing through along the outer wall surface of the second purge gas feed tube 136 are mixed with each other.

In this way, the temperature distribution of the purge gas flowing in the gap 135 becomes uniform. Thus, it is possible to prevent the purge gas flowing in the second purge gas feed tube 136 from being affected by the outside air, and it is thereby possible to make the temperature distribution uniform on the light path of the measurement light. As a result, occurrence of the thermal lens effect phenomenon can be prevented, so that the measurement accuracy can be enhanced.

In the example illustrated in FIG. 13, the gap 135 between the second sleeve 134 and the second purge gas feed tube 136 is also opened toward the flue 150, but it is possible to dispose a blocking plate to the distal end portion thereof. In this case, since an opening is formed in the blocking plate so as to be disposed on the upstream side of the gas flow S than the distal end portion of the second purge gas feed tube 136, it is possible to effectively flow the purge gas that prevents the sample gas from reaching the optical system member.

In addition, by disposing this blocking plate to the distal end portion 145 of the second purge gas feed tube 136, the distal end portion 145 of the second purge gas feed tube 136 can be fixed to the second sleeve 134. Thus, it is possible to prevent the distal end portion 145 of the second purge gas feed tube 136 from being vibrated, and to enhance the measurement accuracy.

A second attachment portion 160 includes a second attachment flange 162 that is disposed on an opening 161 of the pipe side wall 151, for example.

A blocking plate 164 is attached so as to shield a gap 163 between the opening 161 of the second attachment portion 160 and the second sleeve 134.

The blocking plate 164 is disposed in a vicinity of the inner surface 156 of the pipe side wall 151. In this way, because the blocking plate 164 is disposed on the flue 150 side, it is possible to prevent the sample gas from flowing into the gap 163.

The blocking plate 164 is a disk-like member fixed to the outer circumference surface of the second sleeve 134, and the outer circumference rim is close to or contacts with an inner circumferential surface of the opening 161. In the former close case, it is preferred that the gap should be small from viewpoint of shielding the sample gas. In addition, in the latter contacting case, the gap 163 is shielded so that the effect of blocking the sample gas is enhanced.

The illustrated example shows an example where the single blocking plate 164 is attached to the second sleeve 134, but it is possible to dispose a plurality of blocking plates with a space between each other in an axis direction of the second sleeve 134. In this case, it is harder for the sample gas to flow into the gap 163.

In the ninth embodiment, the first unit 110 of the optical system member for emitting and receiving light and the second unit 130 equipped with the optical system members including the reflector are disposed at opposed positions of the pipe side wall 151. In this embodiment, the purge gas prevents the sample gas from reaching the optical system member so as to prevent pollution of the optical system member. In addition, temperature distribution of the purge gas positioned on the light path of the measurement light is uniformed so that occurrence of the thermal lens effect phenomenon can be prevented.

Distal ends of the first sleeve 117 and the second sleeve 134 may protrude from the inner surface 156 of the pipe side wall 151 to the inside of the flue 150. For instance, if a length of the measurement region is set shorter than the inner diameter of the pipe side wall 151, lengths of the first sleeve 117 and the second sleeve 134 are set so that a distance between the distal end portion of the first sleeve 117 and the distal end portion of the second sleeve 134 corresponds to the length of the measurement region.

In this case, the distal end portion 129 of the first purge gas feed tube 120 and the distal end portion 145 of the second purge gas feed tube 136 are at the same positions as the distal end portions of the first sleeve 117 and the second sleeve 134, respectively.

Instead of the partition plate 125 and the partition plate 141 having a disk shape, it is possible to form a helical protrusion on the outer wall surfaces of the first purge gas feed tube 120 and the second purge gas feed tube 136.

The protrusion may have the same structure as that in the eighth example and may contact with the inner wall surfaces of the first sleeve 117 and the second sleeve 134, or it is possible to adopt a structure in which a gap is formed between the protrusion and the inner wall surfaces of the first sleeve 117 as well as the second sleeve 134.

By this protrusion, there is formed a helical gas flowing path in the second gap 144 between the first sleeve 117 and the first purge gas feed tube 120 and in the second gap 135 between the second sleeve 134 and the second purge gas feed tube 136. Thus, the supplied purge gas is introduced into the flue 150 while being stirred in the gas flowing path.

Thus, the temperature of the purge gas after passing through the second gap 144 between the first sleeve 117 and the first purge gas feed tube 120 as well as the second gap 135 between the second sleeve 134 and the second purge gas feed tube 136 becomes uniform, so that the temperature distribution of the purge gas passing through the inside of the first purge gas feed tube 120 and the second purge gas feed tube 136 becomes uniform.

Therefore, since the temperature distribution inside the first purge gas feed tube 120 and the second purge gas feed tube 136 forming the light path of the measurement light becomes uniform, it is possible to prevent occurrence of the thermal lens effect phenomenon and to improve the measurement accuracy.

Also in the case where a light emission portion and the light receiving portion are attached to opposed positions with respect to the pipe side wall, it is possible to constitute the purge gas feed tube to have a double tube structure.

Variation Example A

The purge gas feed tube 26 may be constituted of the first purge gas feed tube including only the path of the measurement light emitted from the light emission portion 15, and the second purge gas feed tube including only the path of the measurement light received by the light receiving portion 16 after passing through the measurement region, which are independent of each other.

In this case, it is necessary to dispose means for supplying the purge gas to the first purge gas feed tube and the second purge gas feed tube, respectively.

In this case, it is possible to decrease a diameter of the tube for supplying the purge gas, and to reduce a flow amount of the purge gas for protecting the optical system member.

Variation Example B

A pipe having an elliptical cross section may be used as the purge gas feed tube 26.

In this case, a diameter of the purge gas flow path can be decreased in accordance with a layout state of the light emission portion 15 and the light receiving portion 16 so that a flow amount of the purge gas for protecting the optical system member can be decreased.

In addition, the purge gas feed tube 26 may have various sectional shapes such as a polygonal shape including a triangular shape and a rectangular shape, and a combination shape of a circle or an ellipse and a polygonal shape.

In this case, it is possible to enhance flexibility of design based on shapes of the probe tube 11 and other members.

Variation Example C

The embodiment described above proposes the double tube structure of the probe tube 11 and the purge gas feed tube 26, but it is possible to insert one or more tube members between the probe tube 11 and the purge gas feed tube 26 to make a multiple tube structure.

In this case, since the thermal insulation function of the gap formed between the tube members keeps the temperature of the purge gas flowing in the purge gas feed tube 26 to be uniform, occurrence of the thermal lens effect phenomenon can be prevented.

Variation Example D

In the embodiment described above, the partition plate 34 and the protrusion 40 are exemplified as an agitation portion, but other shapes may be adopted.

Variation Example E

In the embodiment described above, the inner diameter of the purge gas feed tube 26 is the same along the flow path direction, but it is possible that the purge gas feed tube has a part having a different inner diameter from that of the other part.

Variation Example F

In each embodiment, there is disclosed the gas analyzing apparatus using the laser beam as the measurement light, but the present invention may be applied to a gas analyzing apparatus using other light source.

Other Embodiments

The present invention is not limited to the above-mentioned embodiments, and may be modified variously within a scope of the spirit of the present invention without deviating from the same. In particular, the plurality of embodiments and variation examples described in this specification can be combined arbitrarily as necessary.

For instance, a type of the probe, a type of the gas, a position of the partition plate, the number of partition plates, a shape of the partition plate, a size of the partition plate, a shape of the protrusion, and a pitch of the protrusion can form a combination of variations thereof.

The structure of the present invention can be applied also to a case where the light emission portion and the light receiving portion are disposed at positions opposed with respect to the pipe side wall. For instance, it is possible to adopt a structure in which one of the first unit 110 and the second unit 130 of the fourth embodiment includes the light emission portion, and the other unit includes the light receiving portion.

In this case too, by disposing the double tube structure to each of the unit including the light emission portion and the unit including the light receiving portion, it is possible to prevent the sample gas from reaching the light emission portion and the light receiving portion. Further, by making the temperature distribution of the purge gas be uniform, it is possible to suppress a fluctuation of the measurement light due to occurrence of the thermal lens effect phenomenon, so that the measurement accuracy can be enhanced.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A gas analyzing apparatus comprising:
 a tube-like member that includes a light path through which measurement light is emitted to a predetermined measurement region of sample gas flowing in a pipe and/or through which the measurement light from the measurement region is received, the tube-like member being attached so as to penetrate a pipe side wall;
 an optical system member configured to emit the measurement light to the sample gas in the measurement region and/or to receive the measurement light from the measurement region;
 a purge gas feed portion configured to supply purge gas to a region positioned on a light path of the measurement light between the optical system member and the measurement region; and
 at least one blocking plate disposed at a position so as to suppress the sample gas from flowing into a gap between the tube-like member and the pipe side wall.

2. The gas analyzing apparatus according to claim 1, wherein
 the pipe side wall has a tube-like inner wall surface disposed around the tube-like member so as to define the gap between it and an outer circumferential surface of the tube-like member, and
 the at least one blocking plate is fixed to the tube-like member.

3. The gas analyzing apparatus according to claim 1, further comprising an attachment assist member attached to the pipe side wall and having an inner circumferential surface forming the gap between it and an outer circumferential surface of the tube-like member, and
 the at least one blocking plate is fixed to the inner circumferential surface of the attachment assist member.

4. The gas analyzing apparatus according to claim 1, wherein the blocking plates are arranged along the axial direction of the tube-like member with a space between each other.

5. The gas analyzing apparatus according to claim 1, wherein the purge gas feed portion includes a purge gas feed tube,
 the purge gas feed tube is provided inside of the tube-like member defining a second gap between it and an inner wall of the tube-like member, and
 the purge gas feed tube has a hollow portion including: a purge gas flow path through which the purge gas is supplied to the region between the optical system member and the measurement region; and the optical path for the measurement light.

6. The gas analyzing apparatus according to claim 5, wherein the purge gas flowing through the hollow portion of the purge gas feed tube is a laminar flow.

7. The gas analyzing apparatus according to claim 5, wherein a distal end of the purge gas feed tube is disposed close to an end portion of the measurement region.

8. The gas analyzing apparatus according to claim 5, further comprising a second blocking plate provided at the distal end of the purge gas feed tube, the second blocking plate shielding the second gap from the measurement region.

9. The gas analyzing apparatus according to claims 5, wherein the second gap constitutes a second purge flow path through which the purge gas is supplied to the region between the optical system member and the measurement region,
 the gas analyzing apparatus further comprising an agitation portion disposed in the second gap and configured to agitate the purge gas passing through the second purge gas flow path.

10. The gas analyzing apparatus according to claim 9, wherein the tube-like member is disposed so as to cross a flow path of the sample gas in the pipe so as to introduce the sample gas flowing through the pipe into the measurement region in an inner hollow of the tube-like member,
 the optical system member includes: a first optical system member provided at a first end of the tube-like member, including a light-emitting unit configured to emit a measurement light to the measurement region and a light-receiving unit configured to receive the measurement light that has passed through the sample gas in the measurement region; and a second optical system member having a reflector provided at a second end of the tube-like member and configured to reflect the measurement light from the light-emitting portion toward the light-receiving unit, the gas analyzing apparatus further comprising a distal end portion purge gas feed tube being communicated with the second gap and having a distal end close to the second optical system member, wherein the purge gas is supplied, through the second purge gas flow path and the distal end portion purge gas feed tube, to a vicinity of the second optical system member.

11. The gas analyzing apparatus according to claim 9, wherein the agitating portion includes at least one partition plate provided at an outer surface of the purge gas feed tube and configured to agitate the purge gas passing through the second gap.

* * * * *